United States Patent
Story et al.

(10) Patent No.: US 9,125,888 B2
(45) Date of Patent: *Sep. 8, 2015

(54) CHONDROCYTE THERAPEUTIC DELIVERY SYSTEM

(71) Applicant: DePuy Mitek, LLC, Raynham, MA (US)

(72) Inventors: Brooks J. Story, Franklin, MA (US); M. E. Liesbeth Brown, West Newton, MA (US); Francois Binette, San Francisco, CA (US)

(73) Assignee: DEPUY MITEK, LLC, Raynham, MA (US)

( * ) Notice: Subject to any disclaimer, the term of this patent is extended or adjusted under 35 U.S.C. 154(b) by 230 days.

This patent is subject to a terminal disclaimer.

(21) Appl. No.: 13/719,792

(22) Filed: Dec. 19, 2012

(65) Prior Publication Data

US 2013/0108596 A1 May 2, 2013

Related U.S. Application Data

(60) Division of application No. 13/069,543, filed on Mar. 23, 2011, now Pat. No. 8,354,100, which is a division of application No. 12/328,083, filed on Dec. 4, 2008, now Pat. No. 7,927,599, which is a continuation-in-part of application No. 10/657,516, filed on Sep. 8, 2003, now Pat. No. 7,897,384, and a division of application No. 11/463,714, filed on Aug. 10, 2006, now Pat. No. 8,153,117, which is a division of application No. 10/657,516, filed on Sep. 8, 2003, now Pat. No. 7,897,384, and a division of application No. 11/463,708, filed on Aug. 10, 2006, now Pat. No. 8,394,369, which is a division of application No. 10/657,516, filed on Sep. 8, 2003, now Pat. No. 7,897,384, and a continuation-in-part of application No. 12/123,650, filed on May 20, 2008, now Pat. No. 8,257,963.

(60) Provisional application No. 60/941,326, filed on Jun. 1, 2007.

(51) Int. Cl.
| | |
|---|---|
| A61K 35/32 | (2015.01) |
| C12N 5/077 | (2010.01) |
| A61L 27/38 | (2006.01) |
| A61L 27/54 | (2006.01) |
| A61K 9/00 | (2006.01) |
| A61K 35/12 | (2015.01) |

(52) U.S. Cl.
CPC .............. *A61K 35/32* (2013.01); *A61K 9/0024* (2013.01); *A61L 27/3817* (2013.01); *A61L 27/54* (2013.01); *C12N 5/0655* (2013.01); *A61K 35/12* (2013.01); *A61L 2300/252* (2013.01); *A61L 2430/02* (2013.01); *A61L 2430/06* (2013.01); *C12N 2510/00* (2013.01); *C12N 2533/74* (2013.01); *C12N 2533/76* (2013.01)

(58) Field of Classification Search
CPC ........... A61K 2035/155; A61K 9/0024; A61L 27/3817; A61L 2300/252; A61L 2430/02; A61L 2430/06
See application file for complete search history.

(56) References Cited

U.S. PATENT DOCUMENTS

| | | |
|---|---|---|
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,332,255 A | 6/1982 | Hakim et al. |
| 4,352,883 A | 10/1982 | Lim |
| 4,373,527 A | 2/1983 | Fischell |
| 4,387,715 A | 6/1983 | Hakim et al. |
| 4,551,128 A | 11/1985 | Hakim et al. |
| 4,595,390 A | 6/1986 | Hakim et al. |
| 4,615,691 A | 10/1986 | Hakim et al. |
| 4,642,120 A | 2/1987 | Nevo et al. |
| 4,904,259 A | 2/1990 | Itay |
| 5,041,138 A | 8/1991 | Vacanti et al. |
| 5,053,050 A | 10/1991 | Itay |
| 5,108,753 A | 4/1992 | Kuberasampath et al. |
| 5,283,187 A | 2/1994 | Aebischer et al. |
| 5,464,929 A | 11/1995 | Bezwada et al. |
| 5,468,253 A | 11/1995 | Bezwada et al. |
| 5,554,148 A | 9/1996 | Aebischer et al. |
| 5,595,751 A | 1/1997 | Bezwada et al. |
| 5,597,579 A | 1/1997 | Bezwada et al. |
| 5,607,687 A | 3/1997 | Bezwada et al. |

(Continued)

FOREIGN PATENT DOCUMENTS

| | | |
|---|---|---|
| AU | 2004205266 A1 | 3/2005 |
| CA | 2477164 A1 | 2/2005 |

(Continued)

OTHER PUBLICATIONS

Extended European Search Report for Application No. 08756110.6 issued Feb. 28, 2014 (9 Pages).

(Continued)

*Primary Examiner* — Marcia S Noble

(57) ABSTRACT

Systems and methods for modifying the environment of target cell using genetically altered chondrocytes are provided. The genetically engineered chondrocytes can be used to express a therapeutic agent in a subject, including in an environment typically associated with chondrocytes and in an environment not typically associated with chondrocytes.

12 Claims, 15 Drawing Sheets

(56) References Cited

U.S. PATENT DOCUMENTS

| | | | |
|---|---|---|---|
| 5,618,552 A | 4/1997 | Bezwada et al. |
| 5,620,698 A | 4/1997 | Bezwada et al. |
| 5,645,850 A | 7/1997 | Bezwada et al. |
| 5,648,088 A | 7/1997 | Bezwada et al. |
| 5,698,213 A | 12/1997 | Jamiolkowski et al. |
| 5,700,583 A | 12/1997 | Jamiolkowski et al. |
| 5,773,286 A | 6/1998 | Dionne et al. |
| 5,842,477 A | 12/1998 | Naughton et al. |
| 5,855,619 A | 1/1999 | Caplan et al. |
| 5,859,150 A | 1/1999 | Jamiolkowski et al. |
| 5,869,041 A | 2/1999 | Vandenburgh |
| 5,872,094 A | 2/1999 | Goetinck et al. |
| 5,902,745 A | 5/1999 | Butler et al. |
| 5,939,323 A | 8/1999 | Valentini et al. |
| 5,968,502 A | 10/1999 | Treco et al. |
| 5,980,508 A | 11/1999 | Cardamone et al. |
| 6,001,352 A | 12/1999 | Boyan et al. |
| 6,008,013 A | 12/1999 | Reynolds |
| 6,013,853 A | 1/2000 | Athanasiou et al. |
| 6,048,729 A | 4/2000 | Selden et al. |
| 6,054,288 A | 4/2000 | Selden et al. |
| 6,103,528 A | 8/2000 | An et al. |
| 6,149,902 A | 11/2000 | Artavanis-Tsakonas et al. |
| 6,156,331 A | 12/2000 | Peery et al. |
| 6,165,225 A | 12/2000 | Antanavich et al. |
| 6,224,893 B1 | 5/2001 | Langer et al. |
| 6,261,584 B1 | 7/2001 | Peery et al. |
| 6,287,295 B1 | 9/2001 | Chen et al. |
| 6,303,379 B1 | 10/2001 | Selden et al. |
| 6,306,169 B1 | 10/2001 | Lee et al. |
| 6,361,771 B1 | 3/2002 | Tao et al. |
| 6,365,149 B2 | 4/2002 | Vyakarnam et al. |
| 6,387,693 B2 | 5/2002 | Rieser et al. |
| 6,395,292 B2 | 5/2002 | Peery et al. |
| 6,410,313 B1 | 6/2002 | Kasahara et al. |
| 6,413,511 B1 | 7/2002 | Glorioso et al. |
| 6,455,304 B1 | 9/2002 | Weigel et al. |
| 6,458,889 B1 | 10/2002 | Trollsas et al. |
| 6,472,181 B1 | 10/2002 | Mineau-Hanschke |
| 6,548,249 B1 | 4/2003 | Anderson et al. |
| 6,635,268 B2 | 10/2003 | Peery et al. |
| 7,149,587 B2 | 12/2006 | Wardle et al. |
| 7,897,384 B2 | 3/2011 | Binette et al. |
| 7,927,599 B2 | 4/2011 | Story et al. |
| 8,153,117 B2 | 4/2012 | Binette et al. |
| 8,257,963 B2 | 9/2012 | Binette et al. |
| 8,354,100 B2 | 1/2013 | Story et al. |
| 8,394,369 B2 | 3/2013 | Binette et al. |
| 8,592,201 B2 | 11/2013 | Story et al. |
| 2001/0002392 A1 | 5/2001 | Heinegard et al. |
| 2001/0014475 A1 | 8/2001 | Frondoza et al. |
| 2001/0033857 A1 | 10/2001 | Vyakarnam et al. |
| 2001/0037017 A1 | 11/2001 | Luyten et al. |
| 2001/0051834 A1 | 12/2001 | Frondoza et al. |
| 2002/0003727 A1 | 1/2002 | Hartmann |
| 2002/0006428 A1 | 1/2002 | Mahmood et al. |
| 2002/0009477 A1 | 1/2002 | Mahmood et al. |
| 2002/0037279 A1 | 3/2002 | Vandenburgh |
| 2002/0076810 A1 | 6/2002 | Radice et al. |
| 2002/0094569 A1 | 7/2002 | Yu et al. |
| 2002/0110544 A1 | 8/2002 | Goldberg et al. |
| 2002/0115218 A1 | 8/2002 | Havenga et al. |
| 2002/0142984 A1 | 10/2002 | Brigham et al. |
| 2002/0160471 A1 | 10/2002 | Kisiday et al. |
| 2002/0177224 A1 | 11/2002 | Madry et al. |
| 2003/0012805 A1 | 1/2003 | Chen et al. |
| 2003/0036523 A1 | 2/2003 | Czichos et al. |
| 2003/0064088 A1 | 4/2003 | Carvalho et al. |
| 2003/0077260 A1 | 4/2003 | Mineau-Hanschke |
| 2003/0167054 A1 | 9/2003 | Rosenberg et al. |
| 2003/0181878 A1 | 9/2003 | Tallarida et al. |
| 2004/0236192 A1 | 11/2004 | Necola Shehada et al. |
| 2005/0036945 A1 | 2/2005 | Thomas et al. |
| 2005/0054595 A1* | 3/2005 | Binette et al. .......... 514/44 |
| 2005/0191301 A1 | 9/2005 | Heavner et al. |
| 2006/0030526 A1 | 2/2006 | Liu et al. |
| 2006/0292131 A1 | 12/2006 | Binette et al. |
| 2008/0181954 A1 | 7/2008 | Binette et al. |
| 2008/0299173 A1 | 12/2008 | Story et al. |
| 2009/0162386 A1 | 6/2009 | Story et al. |
| 2010/0114074 A1 | 5/2010 | Perry et al. |
| 2011/0171186 A1 | 7/2011 | Story et al. |
| 2012/0302958 A1 | 11/2012 | Story et al. |
| 2014/0081209 A1 | 3/2014 | Story et al. |

FOREIGN PATENT DOCUMENTS

| | | |
|---|---|---|
| JP | 62198368 A | 9/1987 |
| JP | 62269697 A | 11/1987 |
| JP | 2002524083 T | 8/2002 |
| JP | 2004-260041 A | 9/2004 |
| WO | 95/33511 A1 | 12/1995 |
| WO | 96/34955 | 11/1996 |
| WO | 96/39196 | 12/1996 |
| WO | 99/11789 | 3/1999 |
| WO | 0014261 A1 | 3/2000 |
| WO | 02/074912 | 9/2002 |
| WO | 03/082302 | 10/2003 |
| WO | 03/084477 A2 | 10/2003 |
| WO | 2004/071354 A1 | 8/2004 |
| WO | 2008/150270 A1 | 12/2008 |
| WO | 2007/021964 A2 | 2/2014 |

OTHER PUBLICATIONS

Anderson et. al., (1990) Cancer Res., 50: 1853.
Arai, et al., "Adenovirus Vector-Mediated Gene Transduction to Chondrocytes: In Vitro Evaluation of Therapeutic Efficacy of Transforming Growth Factor-Beta1 and Heat Shock Protein 70 Gene Transduction," 1997, Journal of Rheumatology, vol. 24, pp. 1787-1795.
Baekkeskov et. al., (1990) Nature, 347: 151-156.
Bakay et. al., (1985) Appl. Neurophysol., 48: 358-361.
Bartholomew et al., "Baboon mesencymal stem cells can be genetically modified to secrete hum erythropoietin in vovi," Aug. 2001, Human Gene Therapy, vol. 12, No. 12, pp. 1527-1541.
Baskn et. al., (1994) Life Sci., 54: 471-479.
Bjorklund et. al., (1982) Nature 298: 652-654.
Bohme et. al., (1992) Prog. Growth Factor res., 4: 45-68.
Bohme et al., (1995)Exp. Cell Res., 216: 191-198.
Bookman et. al., (1998) Semin. Oncol., 25: 381-96.
Carelli (1982) Proc. Natl. Acad. Sci., USA 79: 5392-5395.
Carson et. al., (1998) J. Surg. Res., 75: 97.
Castano et al., (1991) J. Clin. Endocr. Metab., 73: 1197-1201.
Corvol et. al., (1980) FEBS Lett., 116. 273-276.
Crabb et. al., (1990) J. Bone Mineral Res., 5: 1105-1 112.
Dotta et. al., (1992) Endocrinology 130: 37-42.
Downie et. al., (1994) Dev. Biol., 162: 195.
Farnum C E, Lee R, O'Hara K, Urban J P G; Volume increase in growth plate chondrocytes during hypertrophy: the contribution of organic osmolytes. Bone 2002;30(4):574-81.
Fueshko et. al., (1994) Dev. Bio., 166: 331-348.
Gelb et. al., (1990) Endocrinology 127: 1941-1947.
Gerstenfeld et. al., (1990) Conn. Tiss. Res. 24: 29-39.
Gillard et. al., (1989) Journal Immunol. Methods., 142: 3826-3832.
Golab et. al., (1998) Ann. Oncol., 9: 63.
Greiss et. al., (1993) Biophysical J., 65: 138-148.
Grisceili et. al., (1998) proc. Natl. Acad. Sci., USA 95: 6367.
Grogan, et al. "Engineering Cartilage for Drug Delivery," Institute of Pathology, University of Bern, Murtenstrasse 31, 3010, Ben Switzerland, 2002.
Hahn et. al., (1984) Endocr. Res., 10: 123-138.
Hamamori et. al., (1995) J Clinical Investigation, 95: 1808-1813.
Hantraye et al., (1990) Exp. Neurol., 108: 91-1014.
Hantraye et. al., (1992) Proc. Natl. Acad. Sci., USA 89: 4187-4191.
Hearing et. al., (1986) J. Immunol., 137: 379.
Himeno, et al., "Impaired Vascular Invasion of CBFA1-Deficient Cartilage Engrafted in the Spleen," Jul. 2002, Journal of Bone and Mineral Research, vol. 17, No. 7, p. 1297-1305.

(56) References Cited

OTHER PUBLICATIONS

International Search Report and Written Opinion of PCT/2008/064481 dated Sep. 23, 2008.
Isacson et. al., (1985) Neuroscience 16: 799-817.
Isacson et. al., (1989) Exp. Brain Res., 75(1): 213-220.
Iwamoto et. al., (1993) Exp. Cell Res. 205: 213-224.
Iwamoto et. al., (1993) Exp. Cell Res., 207: 413-420.
Jorgensen at al. (Immunology Today Trends. Sep. 1998, 19(9): 387-391).
Kanazawa et. al., (1986) Neurosci. Lett., 71: 241-246.
Kato et. al., (1998) Proc. Nat. Acad. Sci., 85: 9552-9556.
Koshiba, T., Clinical Cancer Research, Sep. 2000, V6, p. 3530-3535.
Leboy et. al., (1989) J. Biol, Chem 264:17281-17286.
Leboy et. al., (1994) Microscopy Res. and Technique 28: 483-491.
**Leibson et. al., (1984) Nature, 309: 799.
Lian et. al., (1993) J. Cellular Blochem. 52: 206-219.
Madry, et al., "Efficient lipid-mediated gene transfer to articular chondrocytes," Feb. 2002, Gene Therapy, vol. 7, No. 4, pp. 286-291.
Maurer-Gebhard et. al., (1998) Cancer Res., 58: 2661.
Okada et al (Biol. Pharm. Bull. 1997. vol. 20, No. 3, pp. 255-258).
Osborn et. al., (1995) Proc. Natl. Acad. Sci., USA 92: 8055-8058.
Pacifici et. al., (1991) Exp. Cell Res. 195: 38-46.
Palmer et. al., (1983) Science, 222: 1337-1339.
Roark et. al., (1994) Develop. Dynam., 200; 103-116.
Rosselot et. al., (1994) J. Bone Miner Res., 9: 431-439.
Salgaller et. al., (1998) J. Surg. Oncol., 68: 122.
Schwartz et. al., (1989) J. Bone Miner. Res. 4: 199-207.
Shapiro et. al., (1994) J. Bone Min. Res., 9: 1229-1237.
Smith et. al., (1993) Neuroscience 52: 7-16.
Steinert et al. "Arthritis Research & Therapy," 2007, vol. 9. No. 213, pp. 1-15.
Suda, (1985) Calcif Tissue Int., 37 82-90.
Sullivan et. al., (1994) J. Biol. Chem., 269: 22500-22506.
Takaori-Kondo et. al., (1998) Blood, 91: 4747.
Uludag et al. (Advanced Drug Delivery Reviews. 2000; 42: 29-64).
Verma et al., Gene therapy: twenty-first century medicine. Annu Rev Biochem. 2005;74:711-38.
Wong et. al., (1999) Curr. Opin. Immunol., 11: 643-647.
Yokoo, Naoki, et al., J. Jpn. Orthop. Assoc., 2002, vol. 76, No. 8, p. S946.
Zamir et. al., (1984) Brain Res., 322: 356-360.

* cited by examiner

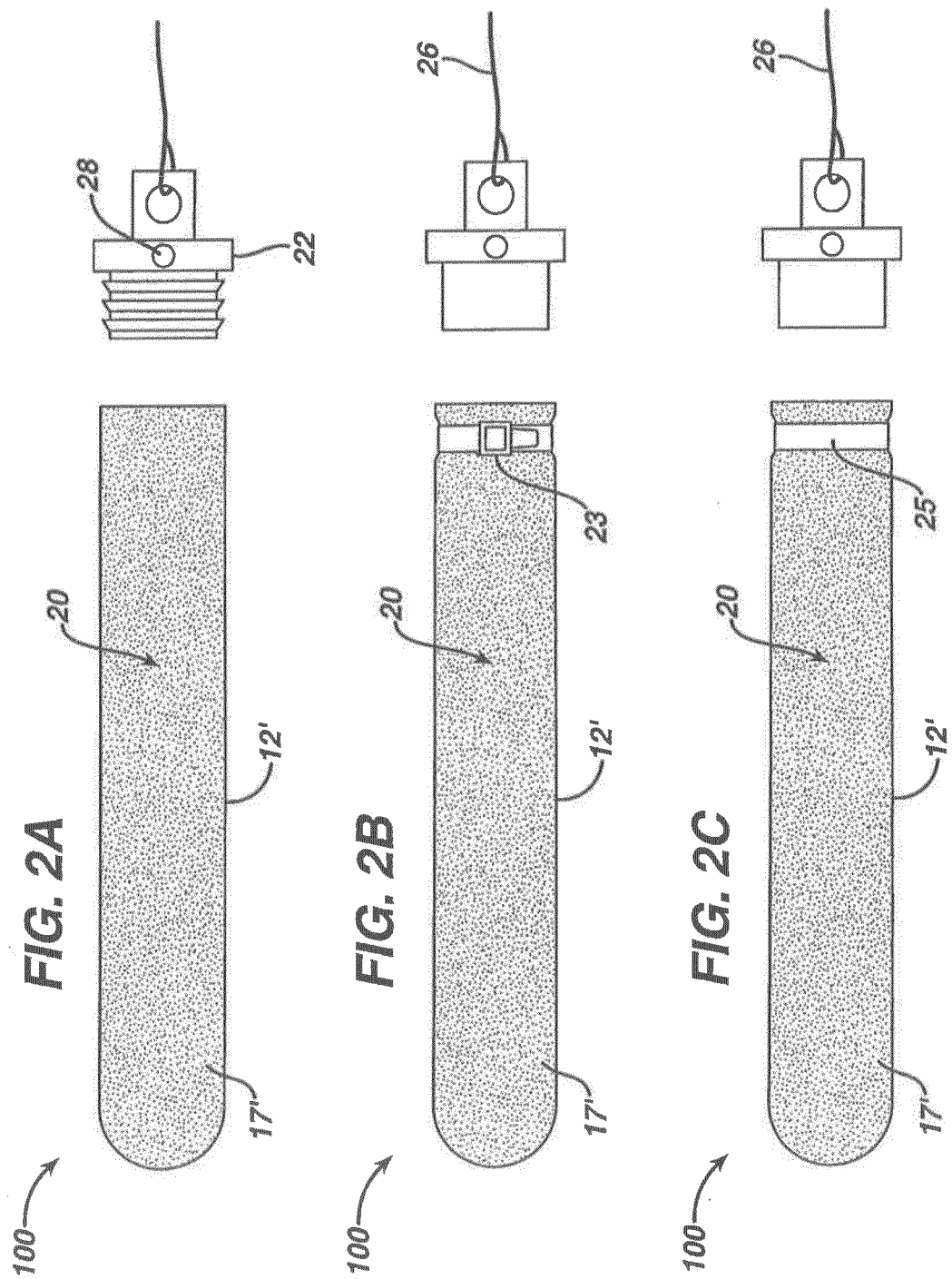

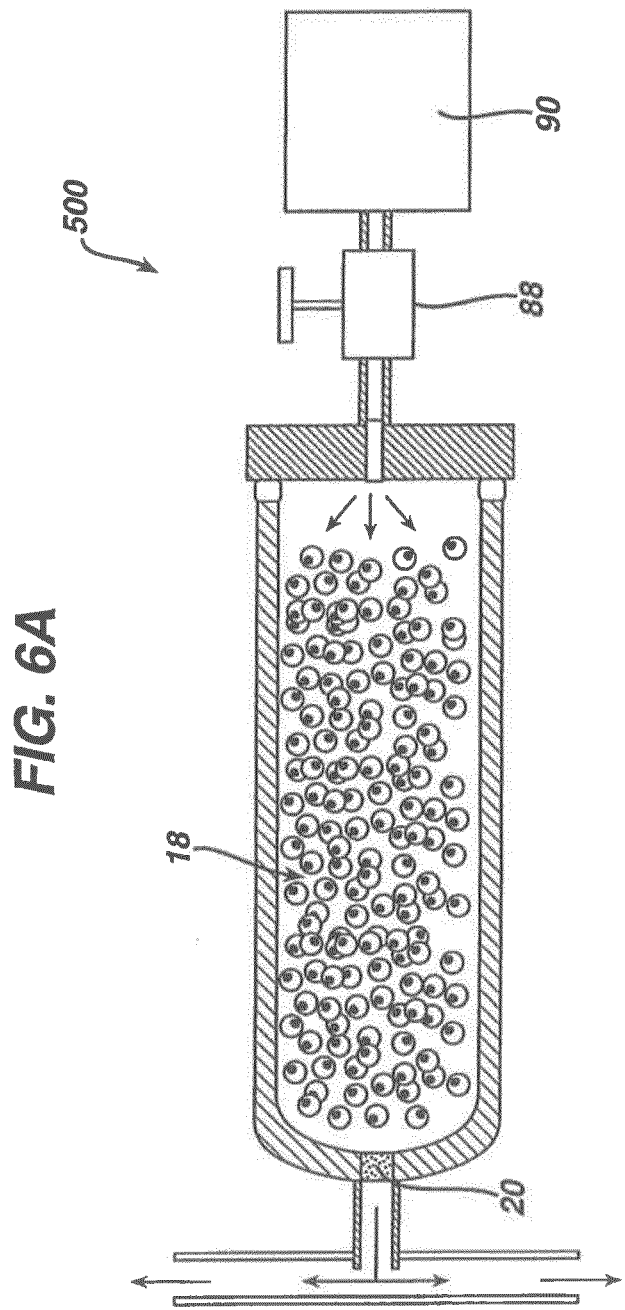

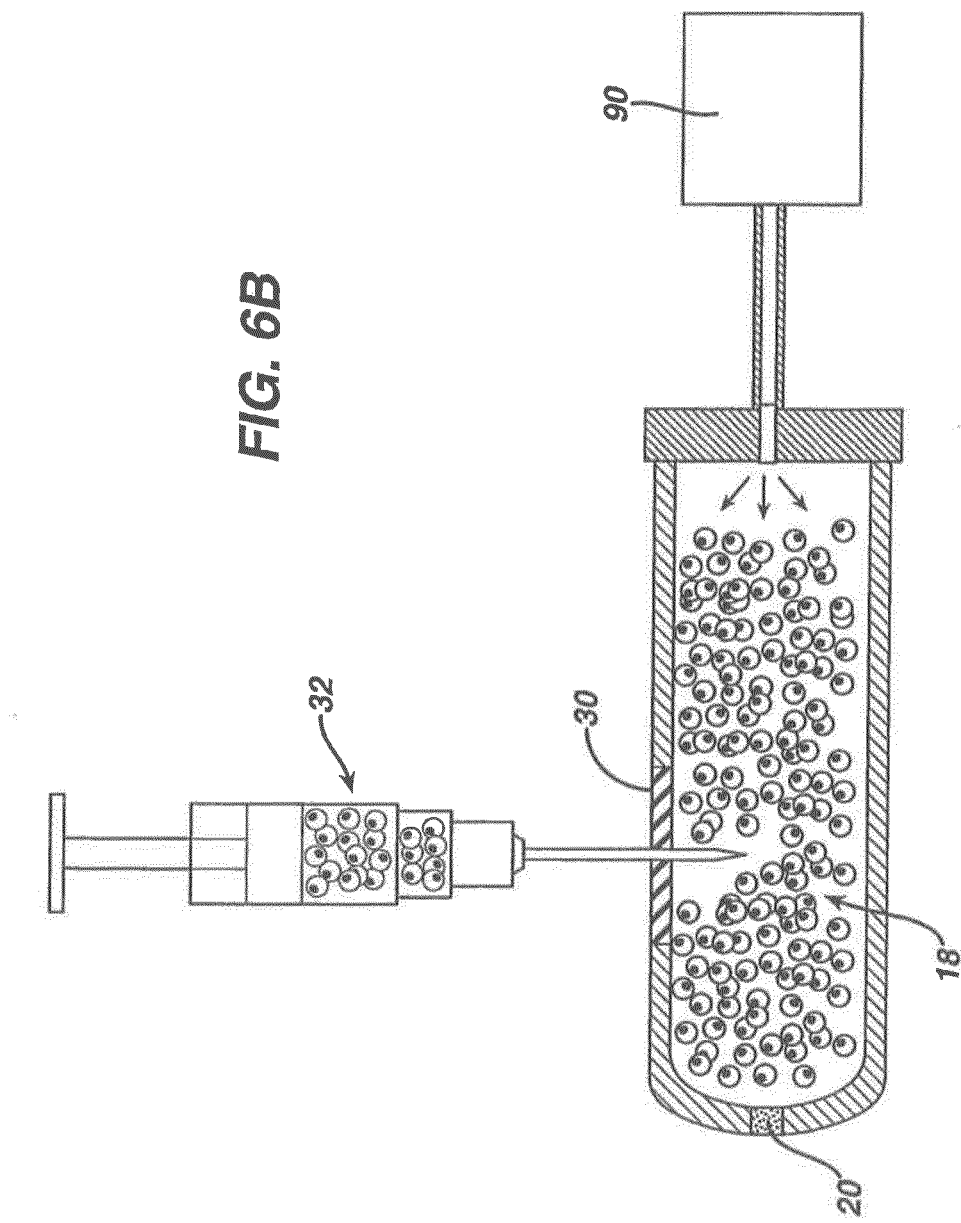

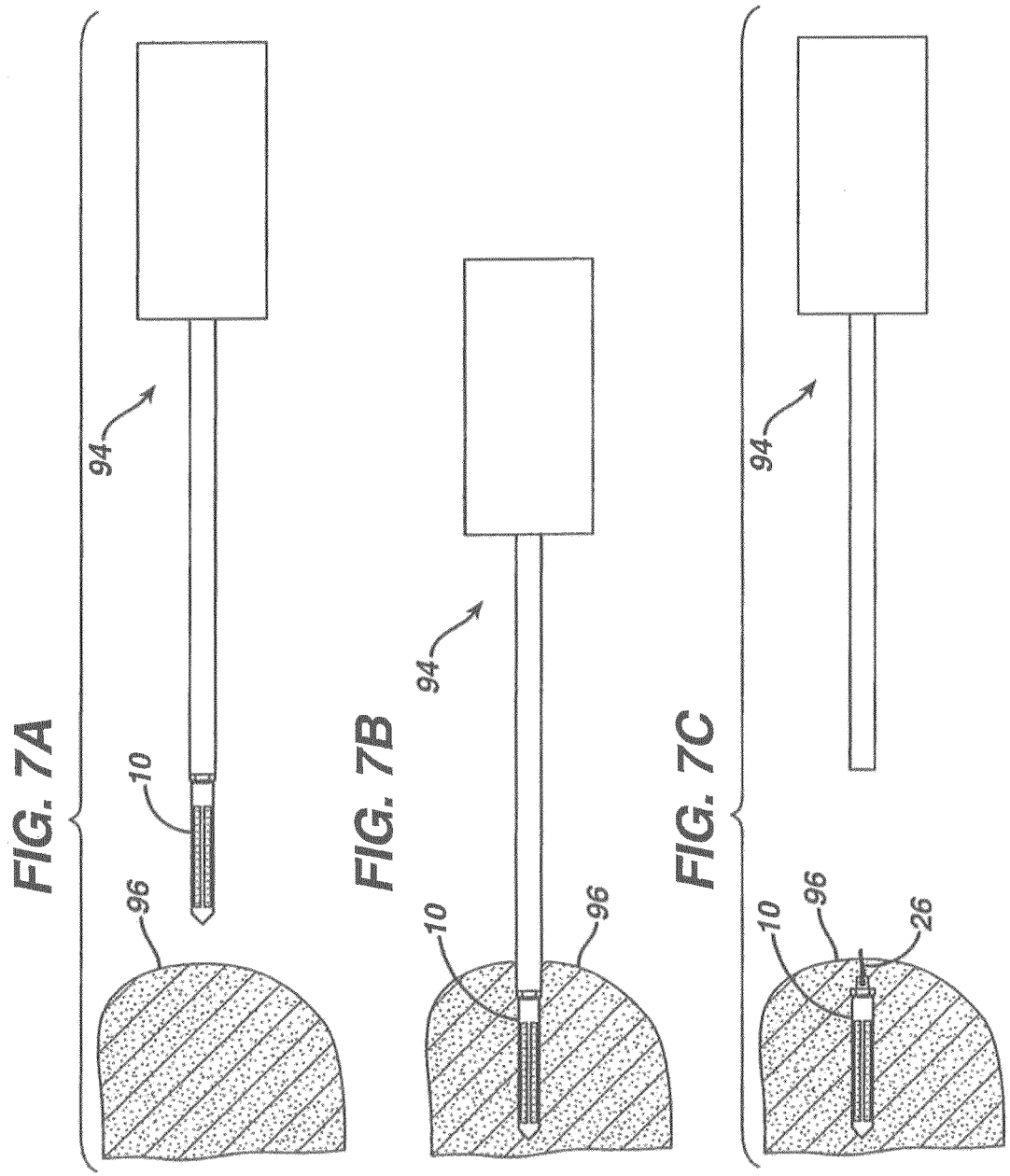

Human articular chondrocytes (HC) encapsulated in alginate in DME/10% FBS or DME/ITS

HC 24 DME 10% FBS

HC 24 DME /ITS

Human ligament cells (ACL) encapsulated in alginate in DME/10% FBS or DME/ITS

ACL DME 10% FBS

ACL DME /ITS

Human fibroblast cells encapsulated in alginate in DME/10% FBS or DME/ITS

FIBROBLASTS DME/10% FBS

FIBROBLASTS DME/ITS

Photograph of cultured bovine chondrocytes

Phase contrast photograph of chondrocytes
transfected with Green Fluorescent Protein (GFP)

Chondrocyte from FIG. 12 showing expression
of Green Fluorescent Protein (GFP)

Graph showing expression of EPO mimetibody from human chondrocytes

FIGS. 15A - C
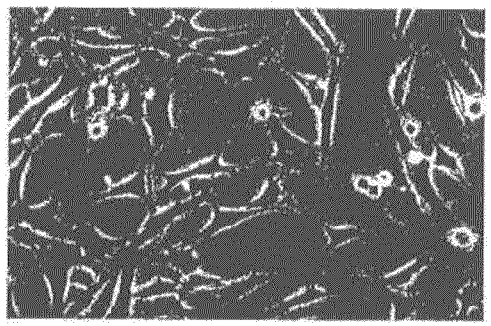
A: Monolayer dedifferentiated cells
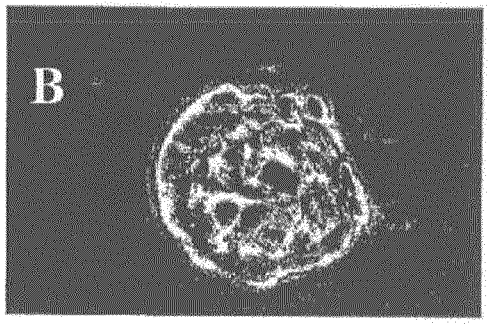
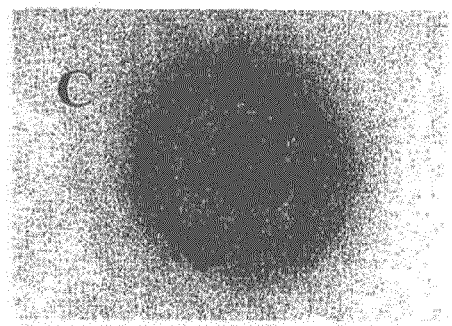
Phase contrast          Alcian Blue Stainig
B and C: Differentiating Chondrocytes in Suspension Culture

CHONDROCYTE THERAPEUTIC DELIVERY SYSTEM

CROSS-REFERENCE TO RELATED APPLICATIONS

The present application is a divisional of U.S. patent application Ser. No. 13/069,543 filed on Mar. 23, 2011 (application pending) and entitled "Chondrocyte Therapeutic Delivery System" which is a divisional of U.S. Ser. No. 12/328,083 filed on Dec. 4, 2008 (now U.S. Pat. No. 7,927,599) and entitled "Chondrocyte Therapeutic Delivery System," which claims priority to and is a continuation-in-part of U.S. patent application Ser. No. 10/657,516 filed on Sep. 8, 2003 (now U.S. Pat. No. 7,897,384) and entitled "Chondrocyte Therapeutic Delivery System," and U.S. patent application Ser. No. 12/123,650 filed on May 20, 2008 (now U.S. Pat. No. 8,257,963) and entitled "Chondrocyte Container and Method of Use," which claims priority to U.S. Provisional Patent Application Ser. No. 60/941,326 filed Jun. 1, 2007. All related applications are incorporated herein by reference in their entirety.

FIELD OF THE INVENTION

This invention relates to the treatment or amelioration of disorders or diseases by the delivery of therapeutic agents(s) produced via genetically-altered chondrocytes chondrocytes to various treatment sites.

BACKGROUND OF THE INVENTION

The use of various types of biologically active cells as components of implanted devices for the purpose of delivering bioactive agents produced by said cells is well known in the art. Various attempts to devise methods for enhancing the survivability of such implanted cells have ultimately fallen short and require either the vascularization of the implant or a maximum diffusion distance of about 2-3 mm in order to provide nutrients to the cells. These various types of cells include fibroblasts, myoblasts, stem cells, progenitor cells, mature differentiated tissue cells, and undifferentiated cells.

Chondrocytes offer several unique advantages as vehicles for expressing therapeutic agents over other cell types. For example, chondrocytes do not require vascular support, and therefore can readily be used in environments that have a reduced, or non-existent vascularization system. Furthermore, chondrocytes are able to survive in harsh in vivo environments, including low pH and low oxygen surroundings. In addition, there is a reduced likelihood of malignancy due to the anti-angiogenic properties of normal chondrocytes. Chondrocytes also possess an immune privileged property which reduces immune rejection of co-implanted allogenic or xenogenic tissue. Furthermore, chondrocytes are more easily scalable compared to other normal untransformed cell strains.

Chondrocytes are typically involved in cartilage repair. Cartilage is a structural support tissue that is found in the body in three main varieties. Hyaline, or articular cartilage, helps dissipate loads in joints. In articular cartilage, chondrocytes are encapsulated in a woven, mesh-like matrix of type II collagen and proteoglycans. Elastic cartilage provides flexible support to external structures, and is composed of chondrocytes embedded in a matrix of collagen and elastic fibers. Fibrocartilage aids in transferring loads between tendons and bone. It consists of an outer layer of collagen and fibroblasts that support and inner layer of chondrocytes that make type II collagen fibers.

To date chondrocytes have been used to correct or repair cartilaginous defects. For example, by placing chondrocytes into hydrogels and injecting the chondrocytes into a cartilage defective region. The chondrocytes are used to express matrix proteins required for cartilage repair. Although chondrocytes have been cultured and placed into substrates such as hydrogels, for treatment, or repair of cartilage or bone defects, there is no teaching in the art that chondrocytes can be used to express therapeutic agents for the treatment of pathologies or injuries other than cartilage tissue.

However, there remains a need for devices and methods capable of delivering a large volume of such genetically-altered chondrocytes to various treatment sites not typically associated with chondroctyes.

SUMMARY OF THE INVENTION

The present invention provides systems and methods for the delivery of genetically altered chondrocytes to various treatment sites to express therapeutic agents. The systems and methods of the invention are particularly conducive to the use of chondrocytes for expressing a therapeutic agent in localized environments that are not typically associated with chondrocytes. Specifically, the genetically altered chondrocytes can be used to express therapeutic agents, such as proteins or antibodies, into localized environments such as the central nervous system (e.g., the brain or spinal cord) or into solid organs (e.g., heart, liver or kidney). This type of localized delivery and expression of the therapeutic agent provides a localized concentration of the therapeutic agent in a particular region, without the necessary side effects that result from systemic administration of the therapeutic agent. In addition, if it is desirable to deliver a therapeutic agent systemically, this can still be done by placing the cells near a vascular structure, including subcutaneously.

Chondrocytes offer several unique advantages as vehicles for expressing therapeutic agents over other cell types. For example, chondrocytes do not require vascular support, therefore can readily be used in environments that have a reduced, or non-existent vascularization system. Furthermore, chondrocytes are able to survive in harsh in vivo environments, including ischemic tissue, as well as low pH and low oxygen surroundings. In addition, there is a reduced likelihood of malignancy due to the anti-angiogenicity properties of normal chondrocytes. Chondrocytes also possess an immune privileged property which reduces immune rejection of co-implanted allogenic or xenogenic tissue. Furthermore, chondrocytes are more easily scalable compared to other normal untransformed cell strains.

The system includes a housing configured to allow passage of a therapeutic agent and at least one genetically altered chondrocyte retained within the housing. As discussed in more detail below, the genetically altered chondrocyte is modified to express a therapeutic agent. The housing defines an internal cell chamber configured to retain genetically altered chondrocytes. While preventing passage of these chondrocytes, the housing can be configured via a number of exit ports (e.g., semi-permeable membranes) to allow for the controlled release of therapeutic agents produced by these entrapped cells. As will be shown in detail below, the cell chamber can be designed such that the core of the chamber can reside a significant distance from the outer wall of the device (e.g., greater than at least about 1.5 mm). Such a large-scale cell chamber can be utilized in light of the chondrocytes' ability to remain viable even when separated from an external nutrient supply. As shown below, the use of such large-scale delivery systems can significantly increase the amount of therapeutic agent(s) capable of being produced and delivered per delivery device. Various aspects of the system and method are summarized below.

In one aspect, a therapeutic system is provided which includes a housing having a cell chamber configured to retain a genetically altered chondrocyte. For example, the cell chamber can have a length and a diameter wherein each the length and the diameter are at least about 3 mm in dimension. These dimensions provide a device capable of producing and delivering a large amount of therapeutic agent to the treatment site. Additionally, a portion of the housing can be configured to allow for passage of the therapeutic agent(s) produced via the chondrocytes from the cell chamber to the treatment site. For example, the housing can include at least one semi-permeable membrane capable of allowing release of the agents. The membrane can be limited to the distal end of the housing, or multiple membranes can be positioned at various locations along the housing (e.g., extending along each side of the housing). Optionally, the housing, or at least a portion thereof, can be made of a porous metal or ceramic material, such that the cells are retained within the housing but proteins are able to pass through the pores.

The housing can be configured to accommodate the desired mode of delivery, treatment site, type of therapeutic agent to be produced, etc. For example, the housing can include a rigid material, a non-rigid material, or any combination thereof. Further, the distal end of the device can include a pointed (or tapered) section configured to facilitate delivery of the device.

The housing can be configured in various manners to allow for delivery (or replenishment) of the chondrocytes to the delivery device. For example, the system can include a cap which can removably couple to an end of the housing such that removing the cap can allow for introduction of the chondrocytes to the cell chamber. In other embodiments, the housing can include an injection port (e.g., a rubber septum) capable of allowing for injection of additional cells via a syringe. In these embodiment, the chondrocytes can be replenished to the device while the device remains at the surgical site thereby significantly increasing efficiency and safety.

In other embodiments, the therapeutic system can include an attachment element (e.g., a suture) coupled to the housing wherein the attachment element is configured to secure the device to tissue/bone at the treatment site. In other embodiments, a radiopaque marker can be disposed on or in the container so as to facilitate positioning and/or locating the housing.

In other embodiments, the housing can include numerous additional chambers so as to enhance efficiency. For example, in addition to the cell chamber, the housing can include an expandable chamber configured to retain a water swellable material wherein the compartments are separated by a piston. In such an embodiment, the introduction of water into the expandable chamber expands the water expandable material thereby forcing the piston to move in a distal direction, and thus forcing an amount of therapeutic agent out of a distal exit port of the cell chamber. Water can be added to the expandable chamber by any number of techniques. For example, the expandable chamber can include an osmotic membrane configured to allow for delivery of water.

In other embodiments, the housing can include an auxiliary fluid chamber positioned between the cell chamber and the expandable chamber. Similar to the embodiment described above, the expandable chamber can include a water swellable material capable of driving a piston in a distal direction upon the introduction of water. However, as opposed to directly acting on the cell chamber, in this embodiment, the piston acts on an auxiliarly fluid retained within the auxiliary fluid chamber. As will be discussed, the auxiliary fluid (which can include cell nutrients, etc.) can be separated from the cell chamber via a semi-permeable membrane. As such, as the piston moves distally, auxiliary fluid is forced through the semi-permeable membrane and into communication with the condrocytes. Ultimately, the desired therapeutic agent(s) are forced out of an exit port (formed, for example, by another semi-permeable membrane) of the cell chamber, and to the treatment site.

In a further aspect, the housing can include a fluid pump and valve system configured to provide a pressurized flow of an auxiliary fluid to the housing from an external reservoir. Additionally, the pump and valve system can provide a continuous outflow of desired therapeutics from the housing to the treatment site. In some embodiments, the pump can be used to remove cells from the housing, and also recharge the container with fresh cells. Also, the pump can be used to infuse the cell chamber of the container with various toxic agents in order to deactive the cells upon completion of the therapeutic regimen.

In some embodiments, the exit port of the housing can be in communication with a delivery tube capable of transporting the therapeutic agents from the cell chamber to one or more distant treatment locations. For example, the delivery tube can include numerous branches so as to allow for delivery of therapeutics along each branch and ultimately to various distinct locations.

The genetically altered chondrocyte can be used to deliver and express therapeutic agents in an environment that requires modification with the therapeutic agent. In one embodiment, the genetically altered chondrocytes can be used to express a therapeutic agent in an environment associated with chondrocytes, such as the cartilage, tendons, joints, and bones. When the genetically engineered chondrocytes are used to express therapeutic agents in environments associated with chondrocytes, they are used for the purpose expressing the therapeutic agent, they do not become part of the structural component of the environment, i.e., they are not used as a component of a tissue engineered construct to repair or replace a damaged cartilage, tendon, joint, or bone. In another embodiment, the genetically altered chondrocytes are used to produce a therapeutic agent at an ectopic site, that is, in an environment that is not typically associated with chondrocytes such as the brain, or solid organs (e.g., heart, kidney, liver). Other atypical chondrocyte environments include an aqueous environment such as blood, and plasma.

The genetically altered chondrocytes can be used to treat or ameliorate a number of disorders by modifying the cell associated with the disorder by expressing the therapeutic agent. The cells associated with a disorder include disorders such as a blood disorder; a cardiovascular disorder; an endocrine disorder; an autoimmune disorder; a neurological disorder; a skin disorder; bone disorder (osteoporosis); a fertility disorder; a metabolic disorder or uncontrolled growth disorder such as cancer. In other embodiments, the genetically altered chondrocytes can also be used to address conditions that are not associated with a disorder, for example, to express a therapeutic agent such as hormones for birth control and reproduction.

Accordingly, in one aspect, the invention pertains to a method of modifying the environment of a target cell associated with a disorder by using a genetically altered chondrocyte to express a therapeutic agent. A housing is provided that is configured to retain the chondrocyte and the housing and genetically altered chondrocyte are delivered to the environment of a target cell associated with a disorder. The genetically altered chondrocyte expresses the therapeutic agent to modify the environment surrounding the target cell.

In one embodiment, the target cell associated with the disorder can be a cell in an atypical chondrocyte environment such as an organ selected from the group consisting of the brain, heart, liver, kidney, gastro-intestinal tract, spleen, smooth muscles, skeletal muscles, eye, ganglions, lungs, gonads, and pancreas. The atypical chondrocyte environment can also be an aqueous environment selected from the group consisting of blood, plasma, the vitreous humor of the eye, spinal fluid, and the like. The genetically altered chondrocyte can be delivered to the spleen, the bone marrow, a ganglion, the peritoneal cavity or any other well vascularized tissue for release into the blood or plasma. In another embodiment, the cell associated with a disorder is in a typical chondrocyte environment such as a bone, tendon and cartilage.

The housing can be configured to accommodate the desired mode of delivery, treatment site, type of therapeutic agent to be produced, etc. For example, the housing can include a rigid material, a non-rigid material, or any combination thereof. Further, a portion of the housing can be configured to allow for passage of the therapeutic agent(s) produced via the chondrocytes from the housing to the treatment site. For example, the housing can include at least one semi-permeable membrane capable of allowing release of the agents The target cell associated with a disorder can be a cell selected from the group consisting of a cell associated with a blood disorder, a cell associated with a cardiovascular disorder, a cell associated with an endocrine disorder, a cell associated with an autoimmune disorder, a cell associated with a neurological disorder, a cell associated with a skin disorder, a cell associated with fertility disorder, and cell associated with reproduction.

Accordingly, in another aspect, the invention pertains to a method for ameliorating a disorder in a subject by implanting a genetically altered chondrocyte retained within a housing into a target region of the subject. The genetically altered chondrocyte expresses the therapeutic agent at a level sufficient to ameliorate the disorder. As discussed above, the housing can include a rigid material, a non-rigid material, or any combination thereof. Further, a portion of the housing can be configured to allow for passage of the therapeutic agent(s) produced via the chondrocytes from the housing to the target region. For example, the housing can include at least one semi-permeable membrane capable of allowing release of the agents.

As will be discussed in more detail below, in one embodiment, the genetically altered chondrocyte is not structurally functional in the target region or an environment surrounding the target region. In one embodiment, the target region is atypical chondrocyte environment such as an organ selected from the group consisting of the brain, heart, liver, kidney, gastro-intestinal tract, spleen, smooth muscles, skeletal muscles, eye, skin, ganglions, lungs, gonads, and pancreas. The atypical chondrocyte environment can also be an aqueous environment selected from the group consisting of blood, plasma, the vitreous humor of the eye, spinal fluid, and the like. The genetically altered chondrocyte can be delivered to the spleen, the bone marrow, a ganglion, the peritoneal cavity or any other well vascularized tissue for release into the blood or plasma. In another embodiment, the cell associated with a disorder is in a typical chondrocyte environment such as a bone, tendon and cartilage.

The injury to be ameliorated can be a wound, a bone defect, a cartilage defect, a skin wound, and a torn ligament. The disorder that can be ameliorated can be a blood disorder, an autoimmune disorder, a hormonal disorder, an anti-inflammatory disorder, a fertility disorder, and an neurodegenerative disorder.

BRIEF DESCRIPTION OF DRAWINGS

FIG. 2A is side view of another exemplary embodiment of the delivery device;

FIG. 2B is a side view of an alternative embodiment of the delivery device of FIG. 2A;

FIG. 2C is a side-view of another alternative embodiment of the delivery device of FIG. 2A;

FIG. 6A is a cross-sectional view of another embodiment of the delivery device;

FIG. 6B is a cross-sectional view of an alternative embodiment of the device of FIG. 6A;

FIG. 7A is side view of an exemplary embodiment of the delivery device being delivered to a treatment site;

FIG. 7B is a side view of the device of FIG. 7A being positioned adjacent the treatment site; and FIG. 7C is a side view of the device of FIG. 7A being secured at the treatment site, and subsequent removal of an insertion tool.

FIG. 15A shows dedifferentiated chondrocytes growing in monolayer;

FIG. 15B is a phase contrast photograph of differentiated chondrocytes; and

FIG. 15C is a photograph of cartilage matrix deposited by the chondrocytes.

DETAILED DESCRIPTION OF THE INVENTION

Figure 1A:
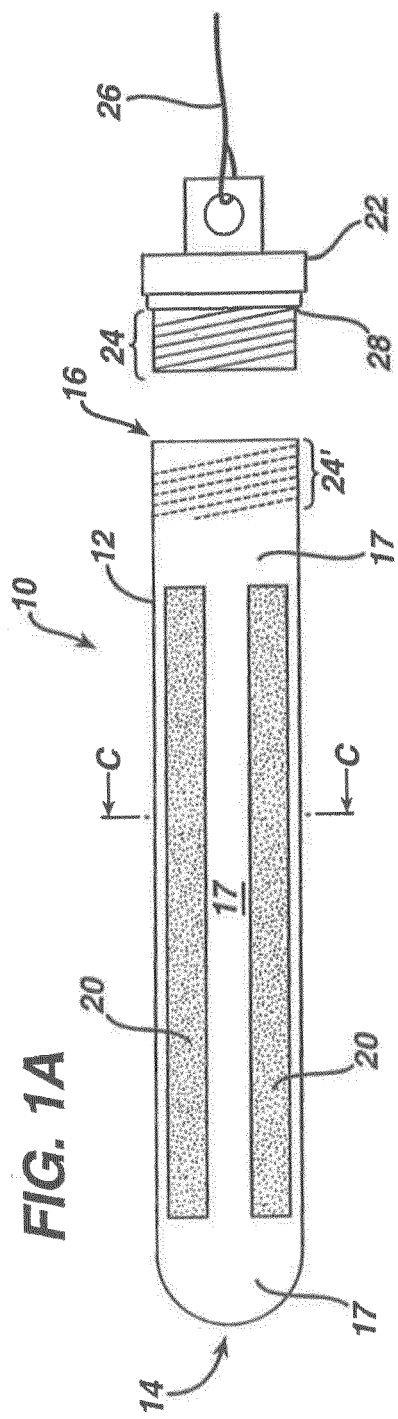
FIG. 1A is a side view of an exemplary embodiment of a delivery device provided herein.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The practice of the present invention employs, unless otherwise indicated, conventional methods of virology, microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.)).

So that the invention may more readily be understood, certain terms are first defined:

The term "chondrocyte" as used herein refers to the art recognized use of the term for a cell type involved in cartilage formation and repair. The chondrocyte functions to produce extracellular matrix of proteoglycans and collagen. Also included with in the use of the term "chondrocyte" are chondrocyte precursor cells such as chondroblasts, and mesenchymal stem cells.

The term "genetically altered chondrocyte" as used herein refers to a chondrocyte cell that has been manipulated using standard molecular biological techniques, in a way that introduces a heterologous or foreign nucleic acid molecule encoding a therapeutic agent into the cell.

The term "nucleic acid" sequence as used herein refers to a DNA or RNA sequence. The term captures sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxymethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, 2-thiocytosine, and 2,6-diaminopurine.

The term "therapeutic agent" as used herein refers to a compound that produces a desired therapeutic effect. The therapeutic agent can be selected from the group consisting of a protein (e.g., short term peptides, bone morphogenic proteins, glycoprotein and lipoprotein), an agonist or an antagonist of an antibody, an antigen, a hormone, an anti-inflammatory agent, an antiviral agent, anti-rejection agents such as immunosuppressants and anti-cancer drugs, an anti-bacterial agent, a growth factor, a cytokine, a hormone, an oncogene, a tumor suppressor, a transmembrane receptor, a protein receptor, a serum protein, an adhesion molecule, a neurotransmitter, a morphogenetic protein, a differentiation factor, an enzyme, matrix proteins, and an extracellular matrix protein, iRNA, RNA, or fragment and peptides thereof. The therapeutic agent include various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-1, IGF-II) and transforming growth factors (e.g., TGF-β I-III), parathyroid hormone, parathyroid hormone related peptide, bone morphogenic proteins (e.g., BMP-2, BMP-4; BMP-6; BMP-7; BMP-12; BMP-13; BMP-14), sonic hedgehog, growth differentiation factors (e.g., GDF5, GDF6, GDF8), recombinant human growth factors (e.g., MP52, (aka rhGDF-5)), cartilage-derived morphogenic proteins (CDMP-1; CDMP-2; CDMP-3). Suitable effectors likewise include the agonists and antagonists of the agents described above. The growth factor can also include combinations of the growth factors described above. If other such substances have therapeutic value, it is anticipated that at least some of these substances will have use in the present invention, and such substances should be included in the meaning of "therapeutic agent" and "therapeutic agents" unless expressly limited otherwise. In a preferred embodiment, the therapeutic agent is protein such as the Erythropoietin (EPO) protein. Other examples of suitable proteins include, but are not limited to, insulin protein, pro-insulin protein, Remicade, bone morphogenetic protein (BMPs), Transforming growth factor-beta (TGF-beta), Platelet-derived growth factor (PDGF), cartilage derived morphogenic protein (CDMP), and MP-52.

In another embodiment, the therapeutic agent is an antibody, an antibody fragment, or a mimetibody. Examples of a useful mimetibody include but are not limited to EPO mimetibody, Remicade mimetibody, BMP mimetibody, cartilage derived morphogenic protein (CDMP) mimetibody and MP-52. In a preferred embodiment, the antibody is the EPO mimetibody.

In yet another embodiment, the therapeutic agent is a growth factor. Preferred growth factors include, but are not limited to, epidermal growth factor, bone morphogenetic protein, vascular endothelial-derived growth factor, hepatocyte growth factor, platelet-derived growth factor, hematopoetic growth factors, heparin binding growth factor, peptide growth factors, and basic and acidic fibroblast growth factors. In some embodiments it may be desirable to incorporate genes for factors such as nerve growth factor (NGF), TGF-beta superfamily, which includes BMPs, CDMPs, GDFs, (Growth differentiation factors), and MP-52. In yet another embodiment, the therapeutic agent is a receptor. Examples of receptors include, but are not limited to, EPO Receptor, B Cell Receptor, Fas Receptor, IL-2 Receptor, T Cell Receptor, EGF Receptor, Wnt, Insulin Receptor, TNF Receptor.

The terms "modifies" or "modified" "modifying" or "modification" are used interchangeably herein and refer to the up-regulation or down-regulation of the therapeutic agent in a cell associated with a disorder, or at a target region. For example, the genetically modified chondrocyte can be used to express a therapeutic agent associated with a blood disorder, e.g., the EPO protein, by delivering the genetically altered chondrocyte to the liver or kidney, or any tissue or organ with a vascular supply to allow EPO to reach the target site or region. Once the EPO protein is expressed, it can enter the circulatory system and bind to, and alter the function of the EPO receptor (EPOR). This in turn will cause a change in the environment associated with the EPO receptor, for example by modifying the signal transduction cascade involving the EPO receptor. Thus, the term "modifies" or "modified" also refers to the increase, decrease, elevation, or depression of processes or signal transduction cascades involving the therapeutic agent (e.g., EPO), or a protein associated with the therapeutic agent (e.g., EPOR).

Modification of the cell may occur directly, for example by overexpressing EPO in a target region. Alternatively, modification of a cell may occur indirectly, for example by the overexpressed EPO interacting with an EPOR that lead to a changes in downstream signal transduction cascades involving the EPOR. Non-limiting examples of modifications include cell proliferation response, cell differentiation, modifications of morphological and functional processes, under- or over-production or expression of a substance or substances by a cell, e.g., a hormone, growth factors, etc, failure of a cell to produce a substance or substances which it normally produces, production of substances, e.g., neurotransmitters, and/or transmission of electrical impulses.

These terms are also used to describe the effect of the expressed therapeutic agent on the cell, the target region, or the environment surrounding the cell or target region. The therapeutic agent is expressed at a level sufficient to produce a desired therapeutic effect by altering the cell, target region, or the environment surrounding the cell or target region. For example, the expression of EPO in a target region, (e.g., the liver), will produce elevated levels of EPO that alter blood hematocrit, and hemoglobin levels.

The phrases "an atypical chondrocyte environment," a "non-chondrocyte typical environment," "an environment not usually associated with chondrocytes," and an ectopic site are used interchangeably herein and refer to a surrounding in which chondrocytes are not present. Examples of an environment not usually associated with chondrocytes include the central nervous system (CNS). The CNS which includes the brain and spinal cord, is generally considered immunoprivileged. Other examples of environments that are not usually associated with chondrocytes include solid organs. Examples of solid organs include, but are not limited to, the heart, kidney, liver and pancreas. Yet another example of an environment not usually associated with chondrocytes, is the reproductive organs. In males, the reproductive organs not associated with chondrocytes are for example, the testis, vas deferens, and the like. In females, the reproductive organs not associated with chondrocytes are, for example, the uterus, fallopian tubes, ovaries and the like. Other examples of an environment not associated with chondrocytes include skin, a subcutaneous pouch, intramuscular and intraperitoneal space.

The term "biocompatible substrate" or "biocompatible matrix" are used interchangeably herein, and refer to a material into, or onto which a cell population (e.g., a chondrocyte population) can be deposited. The material is suitable for implantation in a subject, and does not cause toxic or injurious effects once implanted in the subject.

The term "subject" as used herein refers to any living organism capable of eliciting an immune response. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "vector" as used herein refers to any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

The term "transfection" as used herein refers to the uptake of foreign DNA by a cell. A cell has been "transfected" when exogenous DNA has been introduced inside the cell membrane. Such techniques can be used to introduce one or more exogenous DNA moieties, such as a nucleotide integration vector and other nucleic acid molecules, into suitable host cells. The term captures chemical, electrical, and viral-mediated transfection procedures.

Various aspects of the invention are described in more detail in the following subsections:

I. Culturing and Genetically Altering a Chondrocyte Cell Population

One aspect of the invention pertains to culturing and genetically altering chondrocytes such that the genetically altered chondrocytes express a therapeutic agent. In one embodiment, the genetically altered chondrocytes are used to produce a therapeutic agent in an environment that is not typically associated with chondrocytes, such as the brain, or solid organs (e.g., heart, kidney, liver). In another embodiment, the genetically altered chondrocytes are used to express a therapeutic agent in an environment associated with chondrocytes, such as the cartilage, tendons, joints, and bones. In such instances, the genetically altered chondrocytes are used exclusively for manufacturing and expressing the therapeutic agent, and not as components of a tissue engineered construct used to repair or replace a damaged cartilage, tendon, joint, or bone.

There are a number of reasons for using genetically altered chondrocytes. To begin with, chondrocytes have the ability to survive in very harsh conditions such as environments with a low pH, or low oxygen tension. Thus, the genetically altered chondrocyte population has a post-implantation survival advantage, especially when introduced into diseased or injured tissues such as stroke-damaged tissue.

Furthermore, the genetically altered chondrocytes require no vascular support for survival. This is an important since chondrocytes have a better chance at surviving encapsulation procedures, such as within a gel matrix, as well as implantation procedures. In the past, the size and geometry of cell containing capsules have been limited because most cells depend upon close proximity to vascularity for survival. That is, cells encapsulated in too large a format or in large capsules would have compromised viability because the cells in the center of the implant would not have adequate gas and nutrient exchange.

In addition, chondrocytes have a uniform phenotype. The tissue from which the cells are isolated is mostly composed of chondrocytes, and it is free of vascular endothelial cells, stromal cells or any other cell that forms the cartilage tissue. The physical appearance of the cartilage tissue is also very distinct from the surrounding tissue, making dissection very easy. These characteristics allow for easy isolation of pure population normal chondrocytes. Once the isolated chondrocytes are placed in tissue culture, they behave similarly to fibroblastic cell lines. The fibroblast-like growth is reversible and the cells can be easily induced to redifferentiate into chondrocytes when placed in anchorage independent conditions such as in agarose or alginate gel suspension. Therefore, immortalized transformed cell lines, which are known to be highly metabolic, with a resultant tendency towards cancerous mutation, are not necessary.

Chondrocytes typically secrete an extensive extracellular matrix when placed in anchorage independent conditions This matrix is thought to protect the cells from direct cell-cell contact from the blood supply, thereby delaying or preventing immune rejection. This could provide yet another survival advantage and enable an allogenic or xenogenic implant approach. Allogenic and xenogenic cells could also have a more simple regulatory pathway since they could be seen as temporary, and therefore closer in concept to a device than a permanent tissue transplant.

Furthermore, when the chondrocytes are placed in suspension during anchorage independent culture, they do not need to form an organized tissue to perform because the secretion of extracellular matrix, which protects against rejection, occurs at the cellular level. Large scale preparation of chondrocyte-containing gels could be performed, and the dose of the therapeutic could be adjusted by varying the amount or size of gel to be implanted without affecting the overall behavior of the implant. In other words, a small and large implant would differ only in the number of encapsulated cells, without affecting the biological functioning of the cells.

The chondrocytes can be isolated from a variety of sources. For example, embryonic chondrocytes can be isolated from sterna (Leboy et al., (1989) *J. Biol. Chem.*, 264:17281-17286; Sullivan et al., (1994) *J. Biol. Chem.*, 269:22500-22506; and Bohme et al., (1995) *Exp. Cell Res.*, 216:191-198), and vertebra (Lian et al., (1993) *J. Cellular Biochem.*, 52:206-219), limb bud mesenchymal cells in micromass cultures (Roark et al., (1994) *Develop. Dynam.*, 200:103-116; and Downie et al., (1994) *Dev. Biol.*, 162:195), growth plate chondrocytes in monolayer (Rosselot et al., (1994) *J. Bone Miner. Res.*, 9:431-439; Gelb et al., (1990) *Endocrinology*, 127:1941-1947; and Crabb et al. (1990) *J. Bone Mineral Res.*, 5:1105-1112), or pellet cultures (Kato et al., (1988) *Proc. Nat. Acad. Sci.*, 85:9552-9556) have been used to characterize chondrocyte responses to exogenous factors, many of which function in an autocrine manner.

Chondrocytes can be obtained by a biopsy of cartilaginous tissue from an area treated with local anaesthetic with a small amount of lidocaine injected subcutaneously. The chondrocyte cells from the biopsied tissue can be expanded in culture. The biopsy can be obtained using a biopsy needle, a rapid action needle which makes the procedure quick and simple. In a preferred embodiment, chondrocytes are isolated from donor tissue and large cell banks are carefully characterized and optimized to provide a uniform product.

Chondrocyte cells obtained by biopsy can be cultured and passaged as necessary. For example, articular cartilage can be aseptically obtained from calf knee joints. Cartilage can be shaved from the end of the bones using a scalpel. The tissue can be finely minced in saline solution and submitted to collagenase and trypsin digestion for several hours at 37° C. until the tissue has completely digested and single cells are generated. The chondrocyte cells isolated from the cartilage tissue can then be washed from enzyme with DMEM containing 10% fetal bovine serum, and seeded onto tissue culture plastic dishes using about 5,000 cells to about 10,000 cells per square centimeter. The chondrocyte cells can be cultured in DMEM and 10% fetal calf serum with L-glutamine (292 µg/cc), penicillin (100 U/cc), streptomycin (100 µg/cc) at 37° C. in 5% $CO_2$ with an atmosphere having 100% humidity and expanded in number (See FIG. 1). The chondrocyte cells can then be removed from the tissue culture vessel using trypsin/EDTA and passaged into larger tissue culture vessels or encapsulated in gel suspension. Expanded chondrocyte cells can also be frozen according to standard procedures until needed.

Other sources from which chondrocytes can be derived include adipose-derived cells, mesenchymal stem cells, fetal stem cells, marrow-derived stem cells, and other pluripotent stem cells. The chondrocytes can be autogeneic, isogeneic (e.g., from an identical twin), allogeneic, or xenogeneic.

A number of studies have been conducted on the isolated chondrocytes, from which has emerged the critical role for a number of growth factors, including basic fibroblast growth factor (bFGF), transforming growth factor beta (TGFβ), insulin-like growth factor-1 (IGF-1), and parathyroid hormone (PTH), which regulate chondrocyte proliferation and differentiation. The expression of these factors and their associated receptors are maturation dependent and exquisitely regulated (Bohme, et al., (1992) *Prog. Growth Factor Res.* 4:45-68). Other studies have shown that vitamins A, C, and D are also required for chondrocyte maturation (Leboy et al., (1994) *Microscopy Res. and Technique* 28:483-491; Iwamoto et al., (1993) *Exp. Cell Res.*, 207:413-420; Iwamoto et al., (1993) *Exp. Cell Res.* 205:213-224; Pacifici et al., (1991) *Exp. Cell Res.* 195:38-46; Shapiro et al., (1994) *J. Bone Min. Res.* 9:1229-1237; Corvol et al. (1980) *FEBS Lett.* 116:273-276; Gerstenfeld et al., (1990) *Conn. Tiss. Res.* 24:29-39; Schwartz et al., (1989) *J. Bone Miner. Res.* 4:199-207; and Suda, (1985) *Calcif Tissue Int.*, 37:82-90).

The chondrocyte cells may be engineered to incorporate a nucleic acid encoding a therapeutic agent such as proteins, antibodies, regulators and cytokines. Other molecules, genes, or nucleic acids that influence cell growth, matrix production, or other cellular functions such as cell cycle may also be used. Nucleic acids may be DNA, RNA, or other nucleotide polymers. Such polymers may include natural nucleosides, nucleoside analogs, chemically modified bases, biologically modified bases, intercalated bases, modified sugars, or modified phosphate groups.

In one embodiment, the nucleic acid can be introduced into the chondrocytes as naked DNA, nanocapsules, microspheres, beads, and lipid-based systems such as liposomes, or carriers such as keyhole limpet hemocyanin (KLH) and human serum albumin (See e.g., U.S. Pat. No. 6,303,379, to Selden, incorporated herein by reference).

In another embodiment, the chondrocytes may be transfected using vectors engineered to carry a nucleic acid that encodes the therapeutic agent. The nucleic acid sequences can be cloned into the vector using standard cloning procedures known in the art, as described by Maniatis et al., Molecular Cloning: A Laboratory Manual, Cold Springs Laboratory, Cold Springs Harbor, N.Y. (1982), which is hereby incorporated by reference. Suitable vectors include, but are not limited to plasmid vectors such as pRO-EX (Gibco/BRL), pBR322, pBR325, pACYC177, pACYC184, pUC8, pUC9, pUC18, pUC19, pLG339, pR290, pKC37, pKC101, SV 40, pBluescript II SK⁺ or KS⁺ (See Stratagene Cloning Systems Catalog from Stratagene, La Jolla, Calif., which is hereby incorporated by reference), pQE, pIH821, pGEX, pET series (See Studier et al., Use of T7 RNA Polymerase to Direct Expression of Cloned Genes, Gene Expression Technology vol. 185 (1990), which is hereby incorporated by reference) and any derivatives thereof. In a preferred embodiment, the plasmid vector is pCDNA3.1. In another preferred embodiment, the plasmid vector is pCEP4.

The gene encoding the therapeutic agent (e.g., EPO) can be operably linked to other elements regulating expression of the gene, including, but not limited to, a promoter, an enhancer sequence, repressor sequence, TATA box, transcription stop sequence, ribosomal binding site, post-transcriptional regulatory element, etc. One of skill in the art would appreciate the variety of elements that may be used in combination with the therapeutic gene.

Promoters vary in their "strength" (i.e., their ability to promote transcription), and can be constitutive. For the purposes of expressing a therapeutic gene, it is desirable to use strong promoters in order to obtain a high level of transcription and expression of the therapeutic gene. In one embodiment, the promoter is a constitutive promoter that includes, but is not limited to, CMV, RSV promoters, and the like. Other promoters include, but are not limited to, LTR or SV40 promoter, the *E. coli*. lac or trp, T3 and T7 promoters, HSV thymidine kinase, as well as other promoters known to control expression of genes in prokaryotic or eukaryotic cells. In another embodiment, the promoter is specific for a particular cell type. For example, a promoter is functional in the central nervous system (e.g., glial specific promoters, neuron elonase promoter, and the like); functional in the organs such as the liver (e.g., albumin and alphal antitrypsin promoters, and the like, that are active in hepatocytes); functional in the pancreas (e.g., insulin promoter, pancreatic amylase promoter and the like); or functional in the heart (e.g., ventricular myocyte-specific promoter, alpha-MyHC and beta-MyHC promoter). One skilled in the art will appreciate that the vectors can be readily engineered to include any desired regulatory elements that are required for the specific transcription of the therapeutic gene using standard molecular biology techniques.

Also within the scope of the invention are biologically active fragments of the therapeutic agent that produce a desired effect. For example, the complete gene for EPO can be transfected into a chondrocyte. Alternatively, active fragments of the gene can be used. Thus, the transfected gene may code for the entire therapeutic agent, or for a biologically active peptide. Also within the scope of the invention are homologous proteins that are at least 50, 75, or 90% homologous to the therapeutic agent. Alternatively, a DNA sequence representing a functional peptide agonist could also be used.

A variety of gene transfection techniques are known in the art. The nucleic acid sequence can be introduced into cells via transformation, particularly transduction, conjugation, mobilization, or electroporation. For example, viral vectors such as adenovirus are commonly used to insert DNA into a variety of cells. Other transfection methods include electroporation, calcium-phosphate methods, and lipid based methods. (See e.g., Sambrook et al., Molecular Cloning: A Laboratory Manual, 2nd Ed., 1989; Miller and Calos, eds., Gene Transfer Vectors for Mammalian Cells, 1987; Ausubel et al., eds., Current Protocols in Molecular Biology, 1987; each of which is incorporated herein by reference). Both stable transfection and transient expression techniques may be employed, depending on how long the therapeutic gene should be expressed.

Those chondrocytes that have been genetically altered to carry the plasmid encoding the therapeutic agent, can be selected by any method available to the skilled artisan. In a preferred embodiment, the genetically altered chondrocytes are selected using an antibiotic marker, such as neomycin. This allows for the selection of only those chondrocytes that have been genetically altered. These isolated chondrocytes can then be amplified to provide a population of cells that carries the plasmid encoding the therapeutic agent. These altered chondrocytes retain the phenotype of a typical chondrocytes, but primarily express the therapeutic agent. These genetically altered chondrocyte population does not become a structural part of the cell, target region or the environment surrounding the cell or target region. The genetically altered chondrocytes function only to express the therapeutic agent.

II. Environments and Therapeutic Agents

The invention pertains to using genetically engineered chondrocytes as vehicles to deliver a therapeutic agent to an environment. In one embodiment, the environment can be one that is not typically associated with chondrocytes, such as the central nervous system, or solid organs such as the heart, liver or kidney. In another embodiment, the environment is one associated with chondrocytes, however, the chondrocytes still have the chondrocyte phenotype and they are used expressly to produce the therapeutic agent. The chondrocytes do not perform the function of cartilage tissue (enabling friction-free articulation), and thus they are not used for tissue repair or construction with a tissue engineered construct. In one embodiment, the genetically altered chondrocytes are engineered to express one therapeutic agent, (e.g., EPO). In another embodiment, the genetically altered chondrocytes are engineered more than one therapeutic agents, for example, two therapeutic agents, three therapeutic agents, or more than three therapeutic agents.

The genetically altered chondrocytes can be delivered to a cell or target region using known procedures for delivering vectors. For example, the genetically altered chondrocytes can be mixed with a liquid gel and injected to a target region using a surgical syringe. The liquid gel can solidify in situ at the target region. Alternatively, a chondrocyte-gel matrix solid can be surgically implanted into a target region. The gel matrix solid can be in the form of a thin sheet that can be rolled or folded, and inserted into the target region using a surgical instrument, and allowed to unfold at the target region (e.g., interocular lens). The genetically altered chondrocytes alone (i.e., without being mixed with a substrate), can be injected to a target region.

Examples of environments not typically associated with chondrocytes include, but are not limited to the following:

(i) Central Nervous System

The genetically altered chondrocytes of the invention can be used to ameliorate or modify the function of cells associated with a neurodegenerative or neurological disorder involving the central nervous system. Regions of the central nervous system that can be targeted by the genetically altered chondrocytes of the invention include the cells in the brain and the spinal cord. Examples of therapeutic agents that can be expressed by genetically altered chondrocytes in the central nervous system include, but are not limited to, receptors (e.g. N-methyl-D-aspartate (NMDA) receptor, GluR receptor (e.g., GluR4, GluR6)); neurotransmitters (e.g., dopamine, acetylecholine, and norepharine); transporters (e.g., glutamate transporters such as excitatory amino acid transporters (EAAT)); growth factors (e.g., neurotrophic factor (GDNF), ciliary derived neuronotrophic factor (CNTF), brain derived neuronotrophic factor (BDNF), neuronotrophin-3 (NT3), epidermal growth factor (EGF), fibroblast growth factor (FGF), transforming growth factor-a (TGF-a), transforming growth factor-b (TGF-b), platelet derived growth factor (PDGF)).

a) Suitable Models of Neurodegenerative Diseases (i) Huntington's Disease

The genetically altered chondrocytes of the invention can be used to ameliorate or modify neurodegeneration in a subject with neurodegenerative diseases such as Huntington's disease. Models of Huntington's disease have been developed in several different animals, for example in the rat (Isacson et al. (1985) *Neuroscience* 16:799-817), monkey (Kanazawa, et al. (1986) Neurosci. Lett. 71:241-246), and baboon (Hantraye. et al. (1992) *Proc. Natl. Acad. Sci. USA* 89:4187-4191; Hantraye, et al. (1990) *Exp. Neurol.* 108:91-014; Isacson, et al. (1989) *Exp. Brain Res.* 75(1):213-220). These models of Huntington's disease have been described as providing effective therapeutic models that are predictive of therapeutic efficacy in humans.

Neurodegeneration in Huntington's disease typically involves degeneration in one or both nuclei forming the striatum or corpus stratium, the caudate nucleus and putamen. Administration of the genetically altered chondrocytes that express a therapeutic agent to these regions may modify the function of these regions. The genetically altered chondrocytes may be delivered to these regions using a liquid polymer gel comprising the genetically altered chondrocytes, and delivered using standard stereotactic delivery methods to the specific regions of the brain. The therapeutic effects of expressing the therapeutic agent using genetically altered chondrocytes, can be determined by morphological and immunohistochemical studies. Behavioral tests can also be performed using standard techniques, such as the maze test.

(ii) Parkinson's Disease

Parkinson's disease in humans primarily affects subcortical structures, especially the substantia nigra and loercus caeruleus. It is characterized by the loss of dopamine neurons in the substantia nigra, which have the basal ganglia as their major target organ. Several animal models of Parkinson's disease have been generated in which effective therapies are indicative of therapeutic efficacy in humans. These animal models include three rat models (the rats having lesions in substantia nigral dopaminergic cells caused by treatment with 6-hydroxydopamine, 1-methyl-4-phenyl-1,2,3,6-tetrahydropyridine (MPTP), or surgical transection of the nigral striatal pathway) (See, e.g. Björklund et al. (1982) *Nature* 298:652-654), a rhesus monkey model (the monkeys having lesions in substantia nigral dopaminergic cells caused by treatment with MPTP) (See, e.g., Smith, et al. (1993) *Neuroscience* 52):7-16; Bakay et al. (1985) *Appl. Neurophysiol.* 48:358-361; Zamir. et al. (1984) *Brain Res.* 322:356-360), and a sheep model (the sheep having lesions in substantia nigral dopaminergic cells caused by treatment with MPTP) (Baskin, et al. (1994) *Life Sci.* 54:471-479). In one embodiment, the genetically altered chondrocytes can be modified to express a therapeutic agent (e.g., GABA) that ameliorates, of modifies the function of cells associated with Parkinson's disease. The therapeutic effect can be determined as described above for Huntington's disease.

b) Autoimmune Disorders (i) Diabetes

The genetically altered chondrocytes of the invention can be used to ameliorate or modify autoimmune diseases such as diabetes. A summary of insulin-dependent diabetes mellitus and its animal models is described by Wong et al. (1999) *Curr Opin Immunol* 11:643-647. A few autoantigens have been associated with Type I diabetes mellitus, for example, insulin (Palmer et al. (1983) *Science* 222:1337-1339), glutamic acid decarboxylase (GAD) (Baekkeskov et al. (1990) *Nature* 347: 151-156) and carboxypeptidase H (Castano. et al. (1991) *J. Clin. Endocr. Metab,* 73:1197-1201), and the glycolipids GT3 (Gillard, et al. (1989) *Journal Immunol. Methods* 142: 3826-3832) and GM2-1 (Dotta, et al. (1992) *Endocrinology* 130:37-42) and PM-1 (U.S. Pat. No. 5,908,627). These models can be used to investigate the effect of genetically altered chondrocytes that express a therapeutic agent (e.g., insulin) on diabetes in the animal.

(ii) Rheumatoid Arthritis

The genetically modified chondrocytes of the invention can also be implanted in a patient to treat a disease such as Rheumatoid arthritis. In this embodiment, chondrocytes are implanted either in or close to the joint capsule for the treatment of specific joint that is affected by Rheumatoid arthritis, or in an ectopic site for a systemic delivery to all joints of an anti-inflammatory therapeutic agent. Examples of useful anti-inflammatory therapeutic agents that can be expressed by the genetically modified chondrocytes to treat Rheumatoid arthritis include, but are not limited to TNF-alpha antagonist and Remicade.

(c) Reproduction

Substances involved in reproduction can also be modified using the genetically altered chondrocytes of the invention. Suitable animal models for reproduction are Sprague-Dawley rats, which are readily available. For example, modifying the function of luteinizing hormone-releasing hormone (LHRH), a hormone regulated by the hypothalamus and involved in the stimulation of ovulation and uterine growth (Fueshko et al. (1994) *Dev Biol* 166:331-348; Hahn et al. (1984) *Endocr Res,* 10:123-138). Luteinizing hormone-releasing hormone also plays a role in male sterility by inhibiting the action of luteinizing hormone-releasing hormone with a synthetic decapeptide (Carelli (1982) *Proc Natl. Acad. Sci. USA* 79:5392-5395).

Alternatively, the genetically altered chondrocytes can be used to deliver estrogen for post-menopausal hormone therapy in women. These genetically altered chondrocytes can be delivered to the uterus, fallopian tubes, ovaries and the like reproductive organs. Further, since diffusible factors such as hormones, need not be delivered to a specific target site, unless there is a systemic toxic or unwanted side effect, alternative delivery options include local delivery accomplished by injection through a syringe, surgical implantation, or endoscopic delivery through a trochar. The genetically altered chondrocytes may also be used for sterilization purposes by delivering a sterilization agent that causes sterility in males. The genetically altered chondrocytes that express the sterilization agent can be delivered, for example to the testis. Other male reproductive organs that can be targeted by the genetically altered chondrocytes include, but are not limited to, testis, urethra, and ureter.

(d) Blood Related Disorders

The genetically altered chondrocytes can be used to express therapeutic agents such as erythropoietin (EPO). EPO is a glycoprotein hormone produced primarily by cells of the peritubular capillary endothelium of the kidney, and is responsible for the regulation of red blood cell production. Secondary amounts of the hormone are synthesized in liver hepatocytes of healthy adults. In premature as well as full term infants, the liver is the primary site of EPO production. The kidney becomes the primary site of EPO synthesis shortly after birth. EPO production is stimulated by reduced oxygen content in the renal arterial circulation. Circulating EPO binds to EPO receptors on the surface of erythroid progenitors resulting in replication and maturation to functional erythrocytes by an incompletely understood mechanism.

Clinical conditions that give rise to tissue hypoxia including anemia, lung disease, or cyanotic heart disease, lead to increased levels of serum EPO. Low EPO levels are observed in patients with anemia, patients with cancer, as well as those with rheumatoid arthritis, HIV infection, ulcerative colitis, and sickle cell anemia. Suppression of EPO synthesis by inflammatory cytokines (e.g., IL-1, TNF-alpha) is believed to occur in certain chronic diseases or cancer.

In contrast, elevation of EPO levels can occur in association with renal diseases such as hydronephrosis or cysts, or certain tumors, resulting in erthrocytosis. Examples include renal cell carcinoma (hypernephroma), hepatocellular carcinoma, and adrenal gland tumors. Certain bone marrow disorders, such as myelodysplastic syndrome and aplastic anemia, may also be associated with high serum levels of EPO. In the setting of bone marrow disease, high serum EPO levels are presumably due to the reduction in the number of EPO receptor bearing cells, thereby allowing serum levels to rise. Thus, genetically modified chondrocytes can also be used to express EPO antibody to interact with the elevated EPO to reduce the level.

Suitable in an animal model of anemia that can be used to test the genetically modified chondrocytes are available (See e.g., Hamamori et al., (1995), *J. Clinical Investigation*, 95:1808-1813, Osborne et al., (1995) *Proc. Natl. Acad. Sci., USA*, 92:8055-8058). The genetically modified chondrocytes expressing EPO can be implanted into the anemic animal and determining the level of EPO and the hematocrit of the treated animal can be measured over time.

(e) Allergies

The genetically modified chondrocytes of the invention can also be implanted in a patient to treat allergies by effecting the in vivo production of the allergens, or their antibodies through the genetically modified chondrocytes. Through controlled expression of the allergens, or their antibodies, the patient gradually develops IgG antibodies that block the IgE antibodies which result in long term relief from allergies.

(f) Pain Management

Pain management can be effected through the genetically modified chondrocytes as well by modifying the chondrocytes to express opiates or endorphins. The genetically modified chondrocytes that express such pain mediating substances would be implanted in tissue such as the brain. In addition, the chondrocytes can be modified to express nociceptive pain relievers, and the modified chondrocytes could be implanted locally, at the site of the injury or disease causing pain.

(g) Cancer Treatment

Cancer is a disease that is characterized by uncontrolled growth of abnormal or cancerous cells, in most instances as a result of an altered genome in a single abnormal cell. The alteration in the genome is caused by a mutation in one or more genes wherein the probability of the occurrence of a mutation is increased by a variety of factors including (i) ionizing radiation, (ii) exposure to chemical substances known as carcinogens, (iii) some viruses, (iv) physical irritation, and (v) hereditary predisposition.

The genetically modified chondrocytes can be used to deliver therapeutic agents that enhance a subject's immune response to invading metastases or to either directly or indirectly suppress cancerous cell growth. Such therapeutic agents include, but are not limited to, various cytokines such as interleukin-2 (IL-2), granulocyte-macrophage colony stimulating factor (GM-CSF), interleukin-12 (IL-12) and interferon-gamma (IFN-gamma), anti-angiogenic molecules and tumor associated antigens (Anderson et al., (1990) *Cancer Res.*, 50: 1853, Stoklosa, et al., (1998) *Ann Oncol.*, 9:63, Leibson, et al., (1984) *Nature*, 309:799, Book, et al., (1998) *Semin. Oncol.* 25:381, Salgaller, et al., (1998) *J. Surg. Oncol.*, 68: 122, Griscelli, et al., (1998) *Proc. Natl. Acad. Sci. USA*, 95: 6367).

Suitable models of tumors are available, for example, the mouse tumor model (See e.g., Hearing et al., (1986) *J. Immunol.*, 137: 379). Therapeutic doses of anti-tumor molecules can be delivered in a mouse tumor model using the genetically altered chondrocytes. In vivo tissue or serum levels of recombinant molecules are measured at varying time points following implantation and the effects on tumor development and animal survival are followed over time. Other art-accepted animal models of cancer have been described in Hearing, (1986) *J. Immunol.*, 137:379, Stoklosa et al., (1998) *Ann. Oncol.*, 9:63, Carson et al., (1998) *J. Surg. Res.*, 75:97, Maurer-Gebhard et al., (1998) *Cancer Res.*, 58:2661 and Takaori-Kondo et al., (1998) *Blood* 91:4747).

Therapeutic efficacy of treatment of cancer can be determined by measuring changes in clinical parameters such as tumor shrinkage (e.g. at least 5-10% and preferably 25-100%) and/or extended animal survival time.

(h) Solid Organ Treatment

The genetically modified chondrocytes can be used to deliver therapeutic agents (directly or in close proximity) to a region in a solid organ such as the heart, kidney, or liver.

III. Biocompatible Substrates

The genetically altered chondrocytes of the invention can be delivered to a desired environment by using biocompatible substrates. In one embodiment of the present invention, the substrate can be formed from a biocompatible polymer. A variety of biocompatible polymers can be used to make the biocompatible tissue implants or substrates according to the present invention. The biocompatible polymers can be synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring. In embodiments where the substrate includes at least one synthetic polymer, suitable biocompatible synthetic polymers can include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and blends thereof. Suitable synthetic polymers for use in the present invention can also include biosynthetic polymers based on sequences found in collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of lactide (which includes lactic acid, D-, L- and meso lactide); glycolide (including glycolic acid); $\epsilon$-caprolactone; p-dioxanone (1,4-dioxan-2-one); trimethylene carbonate (1,3-dioxan-2-one); alkyl derivatives of trimethylene carbonate; $\delta$-valerolactone; $\beta$-butyrolactone; $\gamma$-butyrolactone; $\epsilon$-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one;

6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Aliphatic polyesters used in the present invention can be homopolymers or copolymers (random, block, segmented, tapered blocks, graft, triblock, etc.) having a linear, branched or star structure. Poly(iminocarbonates), for the purpose of this invention, are understood to include those polymers as described by Kemnitzer and Kohn, in the Handbook of Biodegradable Polymers, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g., PEO/PLA). Polyalkylene oxalates, for the purpose of this invention, include those described in U.S. Pat. Nos. 4,208, 511; 4,141,087; 4,130,639; 4,140,678; 4,105,034; and 4,205, 399. Polyphosphazenes, co-, ter- and higher order mixed monomer based polymers made from L-lactide, D,L-lactide, lactic acid, glycolide, glycolic acid, para-dioxanone, trimethylene carbonate and, -caprolactone such as are described by Allcock in The Encyclopedia of Polymer Science, Vol. 13, pages 31-41, Wiley Intersciences, John Wiley & Sons, 1988 and by Vandorpe, et al in the Handbook of Biodegradable Polymers, edited by Domb, et al., Hardwood Academic Press, pp. 161-182 (1997). Polyanhydrides include those derived from diacids of the form HOOC—$C_6H_4$—O—$(CH_2)_m$—O—$C_6H_4$—COOH, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in Handbook of Biodegradable Polymers, edited by Domb, et al., Hardwood Academic Press, pp. 99-118 (1997).

As used herein, the term "glycolide" is understood to include polyglycolic acid. Further, the term "lactide" is understood to include L-lactide, D-lactide, blends thereof, and lactic acid polymers and copolymers.

Elastomeric copolymers are also particularly useful in the present invention. Suitable elastomeric polymers include those with an inherent viscosity in the range of about 1.2 dL/g to 4 dL/g, more preferably about 1.2 dL/g to 2 dL/g and most preferably about 1.4 dL/g to 2 dL/g as determined at 25° C. in a 0.1 gram per deciliter (g/dL) solution of polymer in hexafluoroisopropanol (HFIP). Further, suitable elastomers exhibit a high percent elongation and a low modulus, while possessing good tensile strength and good recovery characteristics. In the preferred embodiments of this invention, the elastomer exhibits a percent elongation greater than about 200 percent and preferably greater than about 500 percent. In addition to these elongation and modulus properties, suitable elastomers should also have a tensile strength greater than about 500 psi, preferably greater than about 1,000 psi, and a tear strength of greater than about 50 lbs/inch, preferably greater than about 80 lbs/inch.

Exemplary biocompatible elastomers that can be used in the present invention include, but are not limited to, elastomeric copolymers of ε-caprolactone and glycolide (including polyglycolic acid) with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ε-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Examples of suitable biocompatible elastomers are described in U.S. Pat. No. 5,468,253.

In one embodiment, the elastomer is a copolymer of 35:65 ε-caprolactone and glycolide, formed in a dioxane solvent and including a polydioxanone mesh. In another embodiment, the elastomer is a copolymer of 40:60 ε-caprolactone and lactide with a polydioxanone mesh. In yet another embodiment, the elastomer is a 50:50 blend of a 35:65 copolymer of ε-caprolactone and glycolide and 40:60 copolymer of ε-caprolactone and lactide. The polydioxanone mesh may be in the form of a one layer thick two-dimensional mesh or a multi-layer thick three-dimensional mesh.

In another embodiment, the substrate can be in the form of an injectable gel matrix. The gel matrix can be a biological or synthetic hydrogel, including alginate, cross-linked alginate, hyaluronic acid, collagen gel, fibrin glue, fibrin clot, poly(N-isopropylacrylamide), agarose, chitin, chitosan, cellulose, polysaccharides, poly(oxyalkylene), a copolymer of poly(ethylene oxide)-poly(propylene oxide), poly(vinyl alcohol), polyacrylate, platelet rich plasma (PRP) clot, platelet poor plasma (PPP) clot, Matrigel, or blends thereof.

The gel matrix is selected to have properties that allow the therapeutic agent to be expressed within the gel matrix, as well as allowing the expressed therapeutic agent to diffuse out of the gel matrix into the surrounding environment.

Examples of gel matrices that may be used include, but are not limited to, collagen gel, fibrin glue, polyglycolic acid, polylactic acid, polyethylene oxide gel, alginate or calcium alginate gel, poly-(2-hydroxyethyl methacrylate) (i.e., a hydrogel), polyorthoester, hyaluronic acid, polyanhydride, chitosan, gelatin, agarose, and other bioresorbable and biocompatible materials such as those described in EP 0705878 A2. To promote chondrocyte proliferation and function, the biological gel can additionally contain appropriate nutrients (e.g., serum, salts such as calcium chloride, ascorbic acid, and amino acids) and growth factors (e.g., somatomedin, basic fibroblast growth factor, transforming growth factor-β, cartilage growth factor, bone-derived growth factor, or a combination thereof).

Polysaccharides are a class of macromolecules of the general formula $(CH_2O)n$ which are also useful as the hydrogel substrate in the present invention. Polysaccharides include several naturally occurring compounds, e.g., agarose, alginate and chitosan.

Agarose is a clear, thermoreversible hydrogel made of polysaccharides, mainly the alternating copolymers of 1,4 linked and 3,6-anhydro-α-L-galactose and 1,3 linked β-D-galactose. Two commercially available agaroses are Sea-Prep™ and SeaPlaque™ agarose (FMC Corp. Rockland, Me.). The thermoreversible properties of agarose gels make it possible for agarose to be a liquid at room temperature allowing for easy mixing of cell-gel solution and then cooling to 4° C. causes gelation and entrapment of cells. This is a comparatively benign process, free of chemicals toxic to the cells.

The agarose concentration can be about 0.50 to 2% (w/v), most preferably about 1.0%. In any event, the concentration of agarose should be sufficient to permit chondrocyte encapsulation at a concentration that varies in the range of about $10^4$ cells/ml to $10^7$ cells/ml, and more preferably in the range of about $10^5$ to $10^6$ cells/ml.

Alginate is a carbohydrate polymer isolated from seaweed, which can be crosslinked to form a hydrogel by exposure to a divalent cation such as calcium, as described, for example in WO 94/25080, the disclosure of which is incorporated herein by reference. The modified alginate solution is mixed with the cells to be implanted to form a suspension. Then the suspension is injected directly into a patient prior to crosslinking of the polymer to form the hydrogel containing the cells. The suspension then forms a hydrogel over a short period of time due to the presence in vivo of physiological concentrations of calcium ions (See e.g., U.S. Pat. No. 4,352,883 to Lim, incorporated herein by reference). It is also feasible to form the hydrogel first prior to injection into a patient.

In general, the polymers that make up the biological gels are at least partially soluble in aqueous solutions, such as water, buffered salt solutions, or aqueous alcohol solutions. Methods for the synthesis of the polymers are known to those skilled in the art (See e.g., Concise Encyclopedia of Polymer Science and Polymeric Amines and Ammonium Salts, E. Goethals, editor (Pergamen Press, Elmsford, N.Y. 1980)). Naturally occurring and synthetic polymers may be modified using chemical reactions available in the art and described, for example, in March, "Advanced Organic Chemistry," 4th Edition, 1992, Wiley-Interscience Publication, New York.

Water soluble polymers with charged side groups may be crosslinked by reacting the polymer with an aqueous solution containing ions of the opposite charge, either cations if the polymer has acidic side groups or anions if the polymer has basic side groups. Examples of cations for crosslinking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Several physical properties of the biological gels are dependent upon gel concentration. Increase in gel concentration may change the gel pore radius, morphology, or its permeability to different molecular weight proteins. Gel pore radius determination can be effected by any suitable method, including hydraulic permeability determination using a graduated water column, transmission electron microscopy and sieving spheres of known radius through different agar gel concentrations (See, e.g., Griess et al., (1993) *Biophysical J.*, 65:138-48).

A variety of other suitable biological gels are also known. The polymer can be mixed with cells for implantation into the body and can be crosslinked to form a hydrogel matrix containing the cells either before or after implantation in the body. A hydrogel is defined as a substance formed when an organic polymer (natural or synthetic) is crosslinked via covalent, ionic, or hydrogen bonds to create a three-dimensional open-lattice structure which entraps water molecules to form a gel.

One skilled in the art will appreciate that the volume or dimensions (length, width, and thickness) of the biological gel comprising the chondrocytes can be selected based on the region or environment into which the biological gel substrate is to be implanted. In one embodiment, the biological gel has a length (defined by a first and second long end) of about 10 cm to about 30 cm. The biological gel can further have a length of about 15 cm to about 25 cm. In a preferred embodiment, the biological gel has a length of about 20 cm. In another embodiment, the biological gel has a width (defined by a first and second short end) of about 0.5 cm to about 4.0 cm. The biological gel can further have a width of about 1.0 cm to about 3.0 cm. In a preferred embodiment, the biological gel has a biocompatible substrate with width of about 2.0 cm.

IV. Manufacturing of Therapeutic Agents Using Genetically Altered Chondrocytes

In another aspect, the invention pertains to using the genetically altered chondrocytes for large scale in vitro preparation of therapeutic agents. For example, liter scale production (e.g., several liters) could be effected with expansion and maintenance of chondrocytes on microcarrier beads. Chondrocyte cells could be genetically manipulated to express a therapeutic molecule of commercial value, then expanded and seeded onto microcarrier-bead containing bioreactor. Alternatively, chondrocytes could be seeded directly onto microcarrier beads and expanded directly in bioreactors.

V. Delivery Devices

Various exemplary embodiments of devices and methods adapted to deliver therapeutic agents produced by genetically-altered chondrocytes are provided herein. More specifically, the devices have an external housing which defines an internal cell chamber. The cell chamber is configured to retain a large-volume of chondrocytes while allowing for the release of therapeutic agents produced by these entrapped cells. As will be seen, the cell chamber is sized such that a core of the chamber can be a relatively large distance away from any external nutrient supply thereby utilizing the enhanced viability of chondrocytes to deliver a large volume of cells, and subsequently a large amount of therapeutic agent to the treatment site. More specifically, the cell chamber can be configured such that at least a portion of the cells entrapped therein can be positioned at least about 1.5 mm away from any external nutrient supply. For example, a tubular cell chamber can be sized so as to have both a length and a diameter of at least about 3 mm thereby requiring any external nutrients to diffuse about 1.5 mm to reach the core of the chamber. As will be described below, the release rate of the therapeutic agent can be controlled by positioning various exit ports (e.g., semi-permeable membranes) at various locations relative to the cell chamber. In some embodiments, the entire housing can include such a semi-permeable membrane. In other exemplary embodiments, the housing can define additional chambers capable of interacting with the cell chamber to modify the efficiency of the chondrocytes and/or the rate of release of the therapeutic agents. These components and others are now described in detail.

Figure 1B:
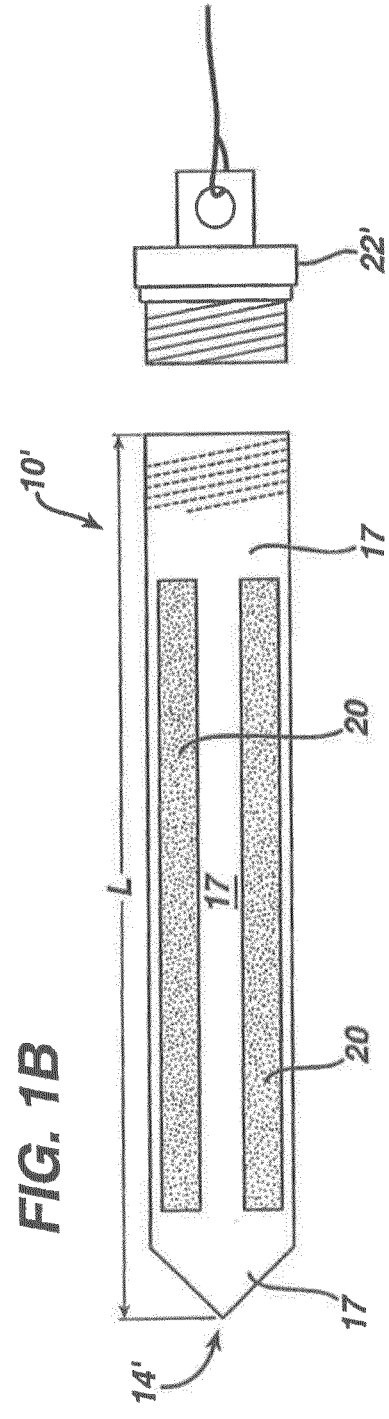
FIG. 1B is an alternative embodiment of the device of FIG. 1A.
Figure 1C:
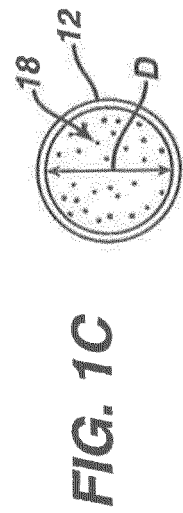
FIG. 1C is a cross-sectional view of the embodiment of FIG. 1A taken along line C-C.
Figure 3:
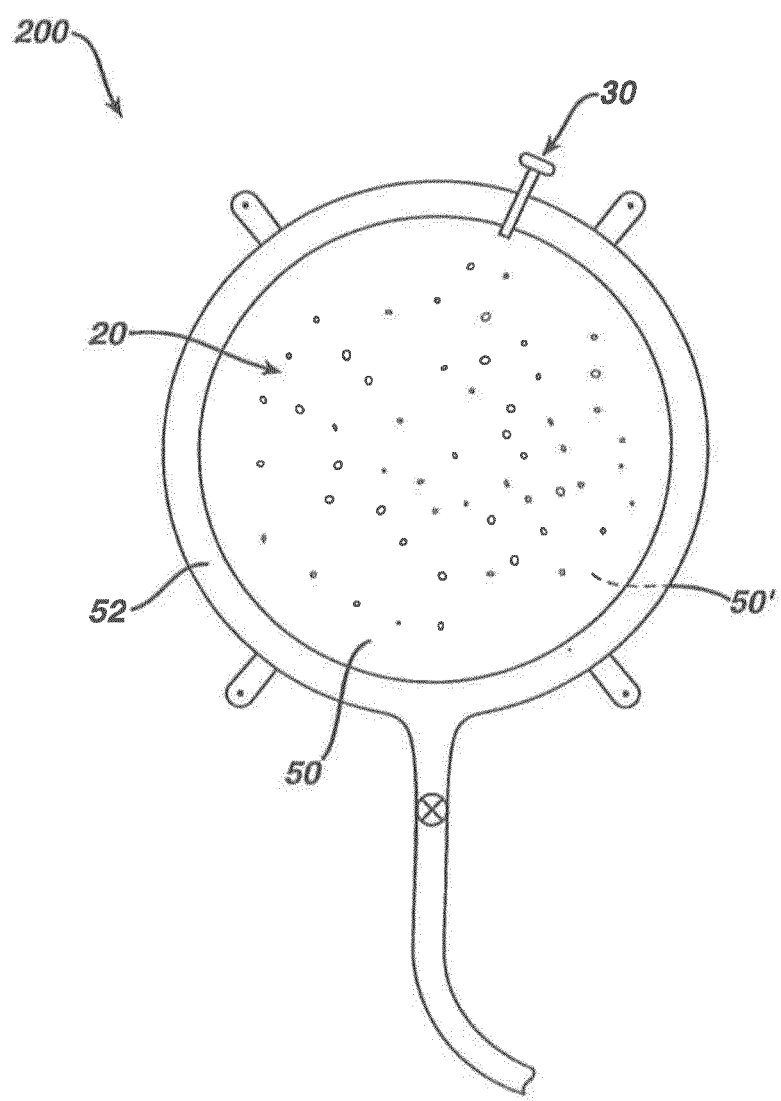
FIG. 3 is a top view of another embodiment of the delivery device.

FIG. 1A provides an exemplary embodiment of a delivery device 10 provided herein. As shown, the device 10 includes a housing 12 having a distal end 14, a proximal end 16, and further defining an internal cell chamber 18 (see FIG. 1C) adapted to retain a plurality of genetically-altered chondrocytes. The housing 12 can include a variety of configurations and/or materials so as to optimize delivery and placement of the delivery device 10. For example, the embodiments of FIGS. 1A and 1B provide a substantially tubular housing 12, and the embodiment of FIG. 3 provides a substantially disc-shaped housing 12. Those skilled in the art will appreciate that various such configurations and/or shapes are within the spirit and scope of the present invention.

Additionally, the housing 12 can include both rigid and non-rigid materials which are selected, sized and positioned to optimize delivery of the device, placement of the device at the treatment site, and, as will be explained in further detail below, release rates of the therapeutic agents produced therein. Referring to FIGS. 1A and 1B, the housing can include a rigid frame 17 configured to allow the delivery device 10 to maintain shape during the therapeutic regimen. Also, as shown in FIG. 1B, the rigid frame 17 can allow for a tapered or pointed distal end 14' configured to facilitate insertion and delivery of the device 10'. Those skilled in the art will appreciate that the rigid frame 18 can be formed from various biocompatible, rigid materials. For example, the materials can include various metals, metal alloys, polymers, combination of polymers, or any combination thereof.

Referring to FIGS. 2A-2C, various embodiments of the delivery device 100 can also include a housing 12' having a non-rigid frame 17'. Use of a non-rigid frame 17' can provide a housing 12' capable of changing configuration during delivery of the device 100 to the treatment site, and/or allowing the housing 12' to substantially adopt the shape of the treatment site upon arrival at the site thereby enhancing delivery of the therapeutic agents. As will be apparent to those skilled in the art, the non-rigid frame 17' of the housing 12' can be formed from a wide-range of biocompatible, non-rigid materials. For example, the non-rigid materials can include various polymers adapted to prevent the passage of both chondrocytes and the therapeutic agents produced therefrom (i.e., a non-permeable membrane).

The delivery device 10 further includes at least one exit port 20 incorporated into the housing 12, and in communication with the internal cell chamber 18. As will be discussed, the exit port 20 is configured to retain chondrocytes within an internal cell chamber 18 while allowing for the release of a therapeutic agent produced via these entrapped cells. The exit port 20 can be any mechanism capable of such selective release of the therapeutic agents. In an exemplary embodiment, the exit port 20 is a semi-permeable membrane. Those skilled in the art will appreciate that any such membrane 20 capable of retaining genetically-altered chondrocytes while allowing for the release of therapeutic agent(s) produced by these entrapped cells is within the spirit and scope of the present invention. For example, the semi-permeable membrane can include a polytetrafluorethylene ("PTFE") membrane with pores ranging from about 0.1 mm to about 0.7 mm. In one embodiment, the pore size is about 0.4 mm to about 0.5 mm. In another embodiment, the pore size is about 0.2 mm.

Exit ports 20 of various sizes, shapes, and/or numbers can be incorporated into the device so as to increase/decrease the release rate of the therapeutic agents. Referring to FIG. 1A, the device 10 includes a first and a second rectangular-shaped exit port 20 extending along a side of the housing 12. FIGS. 2A-2C can include an exit port 20 being incorporated anywhere within the non-rigid housing 12' (indicated generally by an arrow extending towards the housing 12'). For example, the housing 12' can include non-permeable portions and a select area (e.g., the distal tip of the device 100) having a semi-permeable membrane 20 which is adapted to retain chondrocytes while releasing the therapeutic agents produced therein. In other embodiments, the entire housing 12' can be formed from the semi-permeable membrane 20.

Looking at other examples, FIG. 3 provides a disc-shaped housing having a top portion 50, a bottom portion 50', and a central ring 52 joining the top 50 and bottom portions 50'. Similar to the embodiments of FIGS. 2A-2C, the entire top 50 and bottom 50' portions of the device 200 can be formed of a semi-permeable membrane 20, or each portion 50, 50' can include a semi-permeable membrane 20 incorporated into a non-permeable material. In other embodiments, the top portion 50 of the device 200 can be formed of a semi-permeable membrane 20, and the bottom portion 50' can be formed of a non-permeable membrane. Those skilled in the art will recognize that any other combination of semi-permeable and non-permeable membranes are also within the spirit and scope of the present invention.

Referring to the embodiments of FIGS. 4A-6B, the exit port 20 can be incorporated at the distal tip of the device. Such placement of the exit port 20 can allow for the better predictability as to release rate and/or better concentration of the therapeutic agent at the treatment site. Also, use of such a single distal exit port 20 can allow for the therapeutic agent to be delivered directly to a delivery tube 80 for subsequent transport of the agent to various distant locations (as will be discussed below). As will be appreciated by those skilled in the art, embodiments employing a distal exit port 20 can also utilize any number and/or positions of additional exit ports 20 and remain within the spirit and scope of the present invention.

The various housings discussed above each define an internal cell chamber 18 adapted to retain a plurality of genetically-altered chondrocytes. Furthermore, the cell chambers 18 are further in communication with at least one exit port 20 thereby allowing for the release of the therapeutic agents produced via the entrapped cells. As discussed above, the release rate of these therapeutic agents can be modified by changing the number, size, character, pore size, etc. of the exit port 20 in communication with the cell chamber 18. Similar to the above-discussion of the housing, the cell chamber 18 can take various shapes, sizes, and/or configurations. In general, the cell chamber 18 corresponds to the shape of the housing 12 thereby resulting in a cell chamber 18 having a configuration which is tubular (FIGS. 1A-1B), disc shaped (FIG. 3), etc.

As mentioned above, use of chondrocytes allows for a cell chamber 18 capable of retaining a large volume of chondrocytes without being required to minimize the diffusion distance between the core of the cell chamber 18 and an external nutrient supply (i.e., an outer wall of the device). More specifically, in an exemplary embodiment, the cell chamber 18 can be sized such that at least a portion of the chondrocytes retained with the cell chamber 18 can be positioned at least about 1.5 mm from an external source of nutrients. For example, referring to FIGS. 1B (showing a length 'L' of the internal cell chamber 18) and 1C (showing a diameter 'D' of the cell chamber 18), the cell chamber 18 can be sized such that the length (L) and the diameter (D) of the cell chamber 18 are each at least about 3 mm thereby resulting in at least a portion of the cells being at least about 1.5 mm displaced from an external nutrient supply (i.e., the outer housing 12 of the device 10). In other exemplary embodiments, the cell chamber 18 can have a length (L) in the range of from about 100 mm to about 300 mm, and a diameter (D) in the range of from about 3 mm to about 20.0 mm. In other embodiments, the cell chamber 18 can have a length (L) in the range of from about 150 mm to about 250 mm. In another embodiment, the cell chamber 18 has a length (L) of about 200 mm and a diameter (D) of about 10 mm. In another embodiment, the cell chamber 18 has a length (L) in the range of from about 15 mm to about 50.0 mm, and a diameter (D) of from about 10.0 mm to about 30.0 mm.

The delivery device 10 can allow for the introduction of chondrocytes to the cell chamber 18 in a variety of manners. Generally, as introduced to the cell chamber 18, the chondrocytes reside in a gel, gel-like matrix, a liquid suspension, dispersed on a substrate, etc. By way of non-limiting example, the chondrocytes can reside in the biocompatible substrates discussed above in section III. Those skilled in the art will appreciate that chondrocytes in any such form are within the spirit and scope of the present invention. Several examples of such forms which are capable of being utilized are disclosed in assignees co-pending applications U.S. Published Application No. 2005/0054595 and U.S. Published Application No. 2006/0292131, the entirety of these applications being incorporated herein by reference. These applications also detail the preparation of such genetically-altered chondrocytes. Further, the therapeutic agents and examples of potential treatment sites are detailed below in relation to the methods provided herein.

Referring to FIGS. 1A-1B, the delivery device 10, 10' can include a removable cap 22, 22' which allows for introduction of the chondrocyte cells (as indicated in the FIGS. by dots) to the cell chamber 18. As shown in the embodiment of FIG. 1B, the cap 22' can include an head having a series of flats (e.g., a series of flats forming a hexagon shape) which facilitates grasping of the cap by a tool (not shown). Referring to FIG. 1A, the cap 22 can also include a series of grooves 24 adapted to engage a corresponding set of grooves 24' incorporated into an inner wall of the housing 12 thereby allowing the cap 22 to engage or disengage (i.e., screw-on, screw-off) the housing 12. Referring to FIGS. 2A-2C, those embodiments of the device 100 having a housing formed of a non-rigid frame 17' can utilize a compression ring such as a hose clamp 23 or a heat shrink band 25 to engage the cap to the housing 12'. As also shown in the embodiments of FIGS. 1A-1B and 2A-2C, the cap 22 can include additional features such as a radiopaque marker 28 for enhanced visualization of the delivery device 10 once implanted, and/or a suture loop 26 adapted to allow the delivery device 10 to be anchored at the treatment site.

In other embodiments, the delivery device can be adapted to allow for the introduction of chondrocytes (indicated in the FIGS. by circles which are clearly not to scale) into a sealed cell chamber 18 such as when the device 10 is already positioned at the treatment site. For example, as shown in FIGS. 3 and 6B, the delivery device can include a induction port 30 adapted to allow for injection of chondrocytes to the cell chamber 18 via a syringe 32. The induction port 30 an be any mechanism adapted to be pierced by the syringe 32 while remaining capable of maintaining a closed environment. For example, the induction port 30 can be a rubber septum incorporated into the housing 12. Those embodiments of the delivery device 10 utilizing such an induction port 30 can be replenished with new chondrocytes without having to remove the device 10 from the treatment site thereby allowing for enhanced efficiency.

Figure 4A:
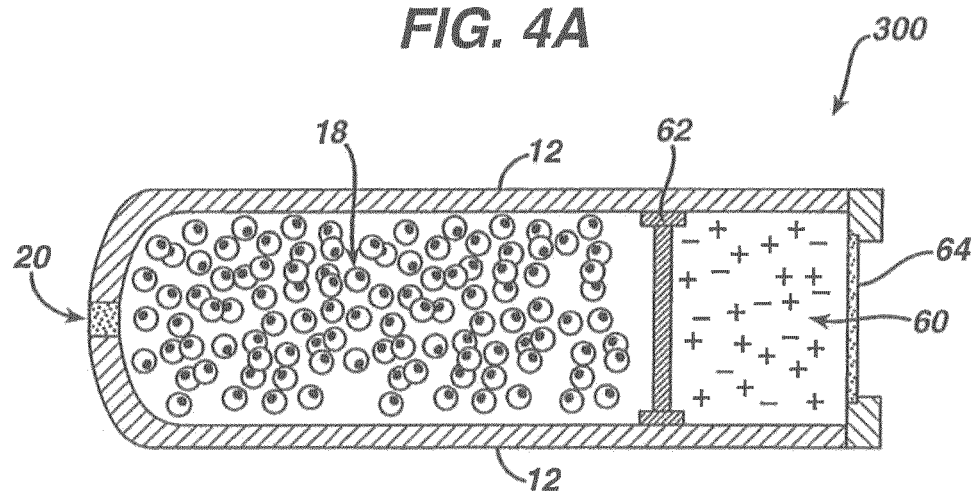
FIG. 4A is a cross-sectional view of another exemplary embodiment of the delivery device wherein a piston element is in a first position.
Figure 4B:
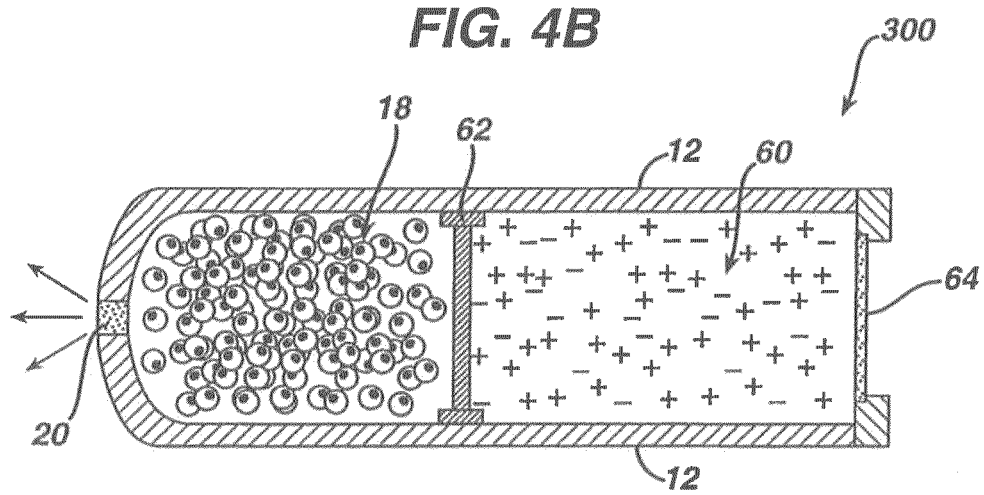
FIG. 4B is a cross-sectional view of the device of FIG. 4A wherein the piston is in a second position.

In other exemplary embodiments, the housing 12 of the device 300 can include various additional chamber(s) so as to control the delivery of the therapeutic agents and/or to provide auxiliary fluids (e.g., cell nutrients, etc.) to the cell chamber 18. Referring to FIGS. 4A and 4B, the housing 12 can define an expandable chamber 60 separated from the cell chamber 18 via a piston 62. The expandable chamber 60 can include a water-swellable agent such that in response to the introduction of water into the expandable chamber 60, the water swellable material expands and drives the piston in the distal direction (as shown in FIG. 4B). As the piston 62 moves distally, the volume of the cell chamber 18 decreases thereby forcing an amount of therapeutic agent out of the distal exit port 20 of the cell chamber 18 (as indicated by a series of arrows).

As will be apparent to those skilled in the art, the water swellable material can be any material cable of expanding in response to the introduction of water. Additionally, as will also be apparent to those skilled in the art, the delivery device 300 can be adapted in various manners so as to allow for the introduction of water to the expandable chamber 60. For example, as shown in FIGS. 4A and 4B, the expandable chamber 62 can include an osmotic membrane 64 adapted to allow for the introduction of water into the expandable chamber 60.

Figure 5A:
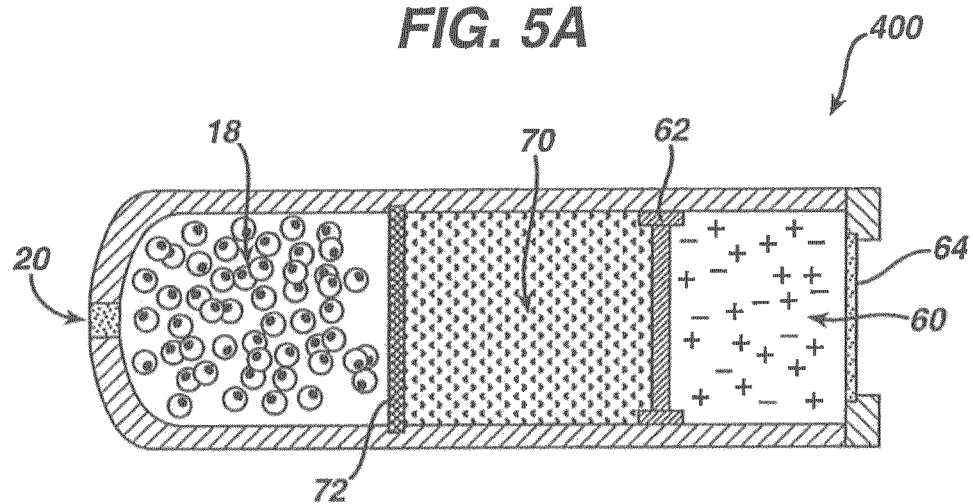
FIG. 5A is a cross-sectional view of another exemplary embodiment of the delivery device wherein a piston is in a first position.
Figure 5B:
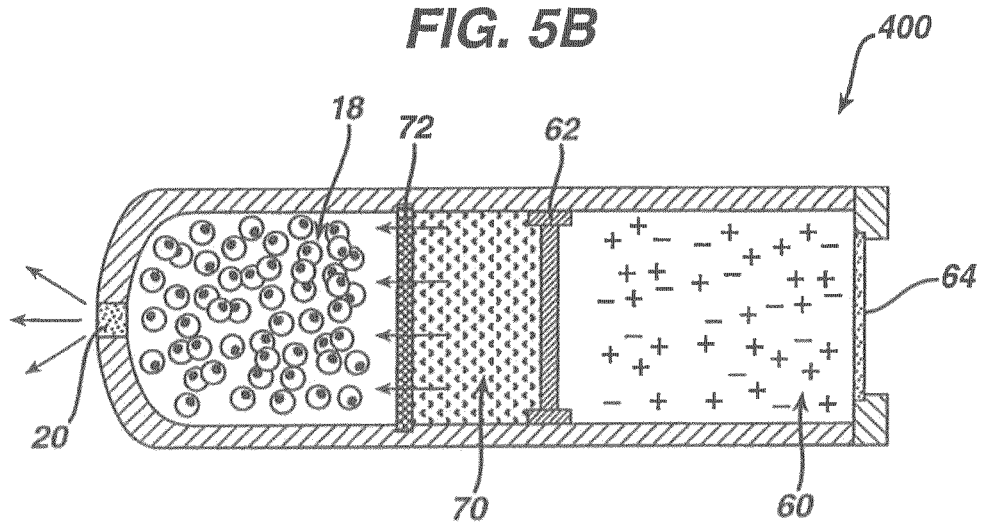
FIG. 5B is a cross-sectional view of the device of FIG. 5A wherein the piston is in a second position.
Figure 5C:
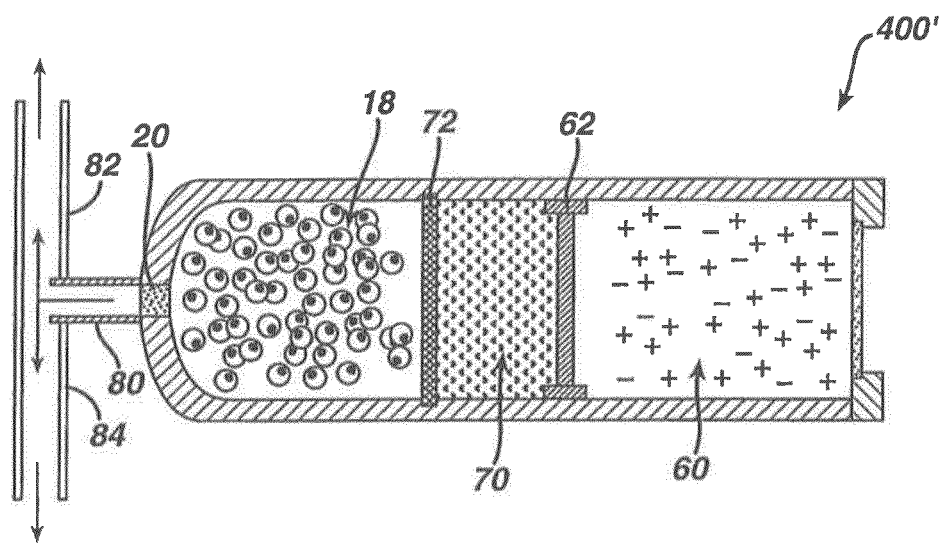
FIG. 5C is a cross-sectional view of an alternative embodiment of the device of FIG. 5A.
Figure 8A:
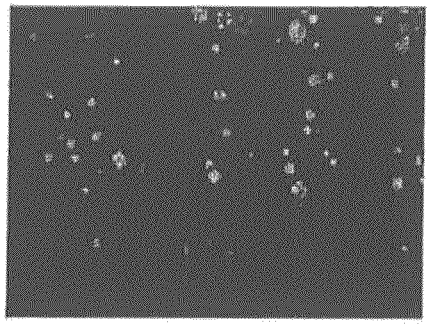
FIG. 8A is a slide showing human articular chondrocytes encapsulated in alginate DME/10% FBS.
Figure 8B:
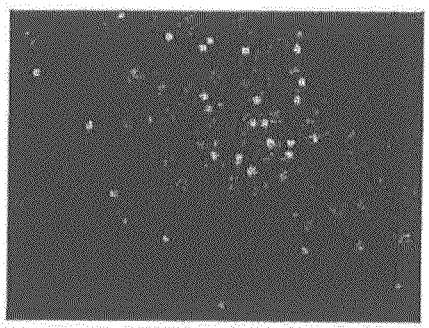
FIG. 8B is a slide showing human articular chondrocytes encapsulated in DME/ITS.
Figure 9A:
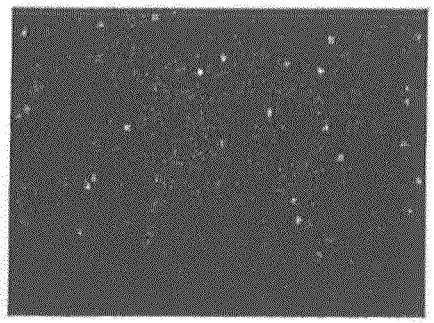
FIG. 9A is a slide showing human ligament cells encapsulated in DME/10% FBS.
Figure 9B:
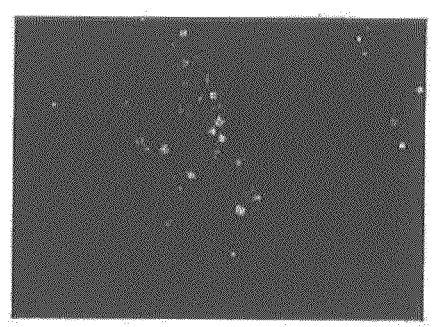
FIG. 9B is a slide showing human ligament cells encapsulated in DME/ITS.
Figure 10A:
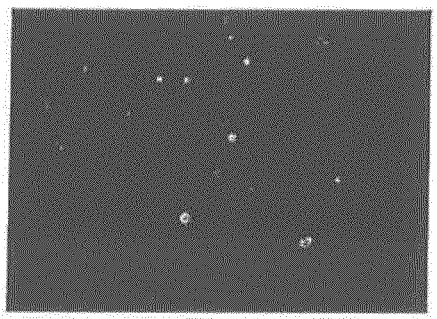
FIG. 10A is a slide showing human fibroblast cells encapsulated in alginate in DME/10% FBS.
Figure 10B:
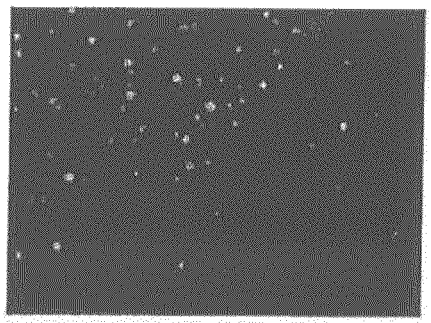
FIG. 10B is a slide showing human fibroblast cells encapsulated in alginate in DME/IT.
Figure 11:
FIG. 11 is a photograph of cultured bovine chondrocytes.

In other exemplary embodiments, the delivery device 400 can include an auxiliary fluid chamber 70 adapted to retain various auxiliary fluids, and deliver these auxiliary fluids to the cell chamber 18. As will be apparent to those skilled in the art, the auxiliary fluid can be any fluid deemed necessary and/or desirable for a given procedure. For example, the auxiliary fluid can include various cell nutrients, or the auxiliary fluid can be any agent capable of modifying or enhancing chrondrocyte performance. Referring to FIGS. 5A-5C, such the auxiliary fluid chamber 70 can be positioned between the cell chamber 18 and the expandable chamber 60. In such an embodiment, as the expandable chamber 60 expands (as discussed above), the piston 62 is driven in the distal direction. However, in this embodiment, the auxiliary fluid chamber 70 can be positioned adjacent the piston 62. As shown, a semi-permeable membrane 72 can be disposed between the auxiliary fluid chamber 70 and the cell chamber 18 such that the auxiliary fluid is controllably introduced to the population of chondrocytes in response to the expanding water-swellable compartment. As shown in FIG. 5B, introduction of the auxiliary fluid to the cell chamber 18 can forces the therapeutic agent(s) out of the distal exit port 20.

In an alternative embodiment, an osmotic pump, such as that of the DUROS device described in U.S. Pat. Nos. 6,287,295; 6,156,331; 6,395,292; 6,261,584; and 6,635,268; the disclosures of which are incorporated by reference, could provide for the flow of therapeutic agent. Optimal control could further be provided for by the HAKIM valve mechanism.

Referring to FIG. 5C, other embodiments of the delivery device 400' can be adapted to deliver the therapeutic agent(s) from the cell chamber 18 to a distal location (i.e., any location not immediately adjacent the exit port 20). As shown, the distal exit port 20 can be coupled to a delivery tube 80 so as to deliver the therapeutic agent to the distal location. As will be apparent to those skilled in the art, the delivery tube 80 can have any dimensions and/or any length capable of being in fluid communication with the exit port 20, and further capable of delivering the therapeutic agent to the desired treatment site. Additionally, the delivery tube 80 can be adapted so to be able to deliver the therapeutic agent to various distant locations. For example, in the embodiment of FIGS. 5C and 6A, the delivery tube 80 include a first branch 82 adapted to deliver a portion of the therapeutic agent to a first distal location, and a second branch 84 adapted to deliver another portion of the therapeutic agent to a second distal location. Those skilled in the art will appreciate that a delivery tube having one or any additional number of such branches is within the spirit and scope of the present invention.

In other embodiments, an external pump 90 and/or valve system 88 can be coupled to the delivery device 500 to provide enhanced control of the delivery of the therapeutic agent from the device 500. Referring to FIG. 6A, an external pump 90 can be coupled to the delivery device 500 via a valve element 88 thereby allowing for continuous pressurized flow of an auxiliary fluid from an external reservoir (not shown). Additionally, introduction of the fluid via the pump 90 can also provide substantially continuous outflow of therapeutic agents from the device 500. Additionally, the pump 90 can be utilized to infuse the cell chamber 18 with various toxic agents so as to deactivate the chondrocytes upon completion of the desired therapeutic regimen. This configuration is somewhat analogous to the HAKIM shunt for hydrocephalitis, except that it is functioning in the reverse direction to actively deliver a fluid into the brain from a reservoir, rather than passively removing a fluid from the brain and draining it into the peritoneal cavity. The valve mechanism of the HAKIM shunt, which is described in U.S. Pat. Nos. 4,332,255, 4,387,715, 4,551,128, 4,595,390, and 4,615,691, the disclosures of which are incorporated herein by reference, could be used to remotely adjust the flow of the therapeutic agent transcutaneously, without the need for additional surgery.

In addition to the embodiments discussed above, a method for delivering therapeutic agents to a treatment site is also provided. As described, the device can contain genetically-altered chondrocytes adapted to produce and release various therapeutic agents. While the chondrocytes are retained within a large-scale cell chamber of the delivery device, various therapeutic agents can be produced within the device via the chondrocytes and delivered to the treatment site via an exit port in communication with the cell chamber.

The method can include disposing a plurality of chondrocytes into the cell chamber of the delivery device. Similar to the embodiments discussed above, the cell chamber can be sized such that a portion of the chondrocytes can be positioned within the cell chamber at a distance of at least about 1.5 mm from an external source of cell nutrients (e.g., a tubular cell chamber having a length and diameter both of which are greater than at least about 3 mm). Further, the cell chamber can be adapted so as to retain the chondrocytes while allowing for the release of a therapeutic agent(s) produced by the chondrocytes. The method further includes delivering the delivery device to a treatment site, and thereafter, delivering the therapeutic agent from the device to the treatment site. In other embodiments, the method can further include suturing the delivery device at the treatment site, and/or injecting additional chondrocytes into the delivery device.

FIGS. 7A-7C provides a representation of the device 10 being delivered to the treatment site 96. As shown in FIG. 7A, the device 10 can be mated to an insertion tool 94. As will be apparent to those skilled in the art, various type of insertion tools 94 can be mated to the device 10 in a wide variety of manners thereby allowing the tool 94 to accurately deliver the device 10 to the treatment site 96. Next, FIG. 7B shows the device 10 being positioned at the treatment site 96. As shown, the device can pierce the treatment site 96 (e.g., a tissue) thereby allowing the device to be disposed substantially within the site 96. As shown in FIG. 7C, the device 10 can then be disengaged from the insertion tool 94, and the tool 94 can be removed from the site 96. Once disengaged, the device 10 can be secured to the site 96 via the suture loop 26, and the device can subsequently deliver various therapeutic agent(s) to the site 96.

Various such therapeutic agents can be produced and released via these genetically-modified chondrocytes. In general, the therapeutic agent can be any compound that produces a desired therapeutic effect. For example, the therapeutic agent can be selected from the group consisting of a protein, an agonist or an antagonist of an antibody, an antigen, a hormone, an anti-inflammatory agent, an antiviral agent, an anti-bacterial agent, a growth factor, a cytokine, an oncogene, a tumor suppressor, a transmembrane receptor, a protein receptor, a serum protein, an adhesion molecule, a neurotransmitter, a morphogenetic protein, a differentiation factor, an enzyme, a matrix protein, an extracellular matrix protein, iRNA, RNA, or fragments and peptides thereof. In an exemplary embodiment, the therapeutic agent is a protein such as the Erythropoietin (EPO) protein. Other examples of suitable proteins include, but are not limited to, insulin protein, pro-insulin protein, Remicade, bone morphogenetic protein (BMPs), Transforming growth factor-beta (TGF-beta), Platelet-derived growth factor (PDGF), cartilage derived morphogenic protein (CDMP), and MP-52.

In another embodiment, the therapeutic agent is an antibody, an antibody fragment, or a mimetibody. Examples of a useful mimetibody include but are not limited to EPO mimetibody, Remicade mimetibody, BMP mimetibody, cartilage derived morphogenic protein (CDMP) mimetibody and MP-52. In a preferred embodiment, the antibody is the EPO mimetibody.

In yet another embodiment, the therapeutic agent is a growth factor. In an exemplary embodiment, the growth factors include, but are not limited to, epidermal growth factor, bone morphogenetic protein, vascular endothelial-derived growth factor, insulin-like growth factor (IGF), hepatocyte growth factor, platelet-derived growth factor, hematopoietic growth factors, heparin binding growth factor, peptide growth factors, and basic and acidic fibroblast growth factors. In some embodiments it may be desirable to incorporate genes for factors such as nerve growth factor (NGF), muscle morphogenic factor (MMP), or TGF-beta superfamily, which includes BMPs, CDMP, and MP-52. In yet another embodiment, the therapeutic agent is a receptor. Examples of receptors include, but are not limited to, EPO Receptor, B Cell Receptor, Fas Receptor, IL-2 Receptor, T Cell Receptor, EGF Receptor, Wnt, Insulin Receptor, TNF Receptor.

In other examples, the genetically modified chondrocyte can be used to express a therapeutic agent associated with a blood disorder, e.g., the EPO protein, by delivering the genetically altered chondrocyte to the liver or kidney, or any tissue or organ with a vascular supply to allow EPO to reach the target site or region. Once the EPO protein is expressed, it can enter the circulatory system and bind to, and alter the function of the EPO receptor (EPOR). This in turn will cause a change in the environment associated with the EPO receptor, for example by modifying the signal transduction cascade involving the EPO receptor.

Modification of the tissue may occur directly, for example by over expressing EPO in a target region. Alternatively, modification of a tissue may occur indirectly, for example by the over expressed EPO interacting with an EPOR that leads to changes in downstream signal transduction cascades involving the EPOR. Non-limiting examples of modifications include cell proliferation response, cell differentiation, modifications of morphological and functional processes, under- or over-production or expression of a substance or substances by a cell, e.g., a hormone, growth factors, etc., failure of a cell to produce a substance or substances which it normally produces, production of substances, e.g., neurotransmitters, and/or transmission of electrical impulses.

As mentioned, the delivery device must be initially delivered to the treatment site. The device can be implanted subcutaneously through a simple incision in the skin. Alternatively, the device can be surgically implanted into a target region using standard surgical methods such as open surgery, or more preferably by minimally invasive surgical methods, such as by using a trocar.

In general, the treatment site can be any site wherein a therapeutic agent can provide a therapeutic benefit. In an exemplary embodiment, the treatment site is an atypical chondrocyte environment (i.e., an environment not usually associated with chondrocytes). Examples of an environment not usually associated with chondrocytes include the central nervous system (CNS), which includes the brain and spinal cord. Other examples of environments that are not usually associated with chondrocytes include solid organs. Examples of solid organs include, but are not limited to, the heart, kidney, liver and pancreas. Yet another example of an environment not usually associated with chondrocytes are the reproductive organs. In males, the reproductive organs not associated with chondrocytes are, for example, the testis, vas deferens, and the like. In females, the reproductive organs not associated with chondrocytes are, for example, the uterus, fallopian tubes, ovaries and the like. Other examples of an environment not associated with chondrocytes include the blood, plasma, cerebrospinal fluid (CSF), skin, a subcutaneous pouch, intramuscular and intraperitoneal space.

The following examples are illustrative of the principles and practice of this invention. Numerous additional embodiments within the scope and spirit of the invention will become apparent to those skilled in the art.

EXAMPLES

Example 1

In Vitro Isolation and Culturing of Chondrocyte Cells

This example describes one of many possible methods of isolating and culturing chondrocyte cells. Articular cartilage was aseptically obtained from calf knee joints. Cartilage was shaved from the end of the bones using a scalpel. The tissue was finely minced in saline solution and submitted to collagenase and trypsin digestion for several hours at 37° C. until the tissue was completely digested and single cells were generated. The chondrocyte cells isolated from the cartilage tissue were then washed from enzyme and seeded onto tissue culture plastic dishes at a concentration of about 10,000 cells/cm$^2$. The chondrocyte cells where expanded in 10% FBS containing DMEM culture medium. Following expansion, the chondrocytes can be released from the vessel using a trypsin/EDTA treatment, centrifuged and concentrated or diluted to a desired concentration to achieve for example a seeding density of approximately 5,000 cells to about 10,000 cells per square centimeter when plated onto culture dishes. Alternatively, the expanded chondrocytes cells can be frozen according to standard procedures until needed.

Example 2

In Vitro Transfection of Chondrocyte Cells and Expression of a Marker Protein This example described the techniques used to transfect chondrocytes with a marker protein, Green fluorescent protein (GFP). A DNA vector carrying a reporter gene is used to establish proof of concept for the utility of normal articular chondrocytes as a drug delivery system for therapeutic application in ectopic sites. As a model, a DNA vector (pTracer-SV40) carrying a gene for green fluorescent protein was used as a surrogate to model a protein not normally present in chondrocytes, and of therapeutic value. If chondrocytes can be transfected by the model vector and expressed the foreign protein, it would demonstrated the ability of using this system for therapeutic protein. In the following example, a lipid formulation from Stratagene (GeneJammer) was used to introduced the foreign DNA into chondrocytes. Any other reagent or physical means of introducing DNA into cell would serve the same purpose.

Exponentially growing chondrocytes were seeded onto 35 mm dishes at a density of 1.5 to 3.7×10$^6$ cells in 10% FBS containing DMEM. In separate plastic tube, serum-free medium was combined with transfection reagent (GeneJammer from Stratagene) and incubated with the chondrocytes for 5-10 minutes. Plasmid DNA (pTracer-SV40 from Invitrogen) was mixed with the chondrocytes, and the mixture further incubated for 5-10 minutes. The transfection mixtures was then added to the 35 mm dishes and incubated for at least 3 hours at 37° C. Fresh media (10% FBS containing DMEM) was then added and the cells are fed every 2-3 days with fresh serum containing media.

Figure 12A:
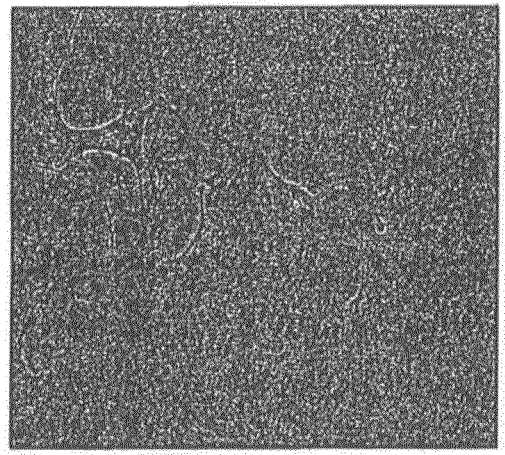
FIG. 12A is a phase contrast photograph of chondrocytes transfected with Green Fluorescent Protein (GFP)
Figure 12B:
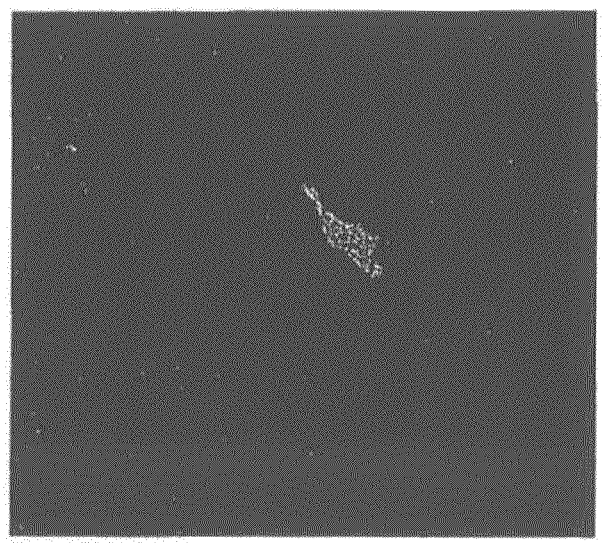
FIG. 12B is a chondrocyte from FIG. 2A showing expression of Green Fluorescent Protein (GFP)

In order to identify transfected chondrocytes, the culture chondrocyte cells were observed under fluorescent light. To facilitate this, the culture media was removed and replaced with phosphate buffered saline solution. The cultured chondrocyte cells were examined by fluorescence microscopy. Positive chondrocyte cells were identified as those that incorporated the plasmid, expressed GFP, and fluoresced green under the microscope, as shown in FIG. 12.

The results illustrate the ability of introducing and expressing a foreign protein in articular chondrocytes. These results further show that chondrocytes provide a robust, stable cell for expression of a heterologous protein.

Example 3

In Vitro Transfection of Human and Bovine Chondrocyte Cells and Expression of EPO Protein This example describes the techniques used to transfect chondrocytes with a therapeutic agent, human erythropoietin (EPO).

An EPO vector was generated which comprised the EPO gene (Genbank Accession No. 182198) inserted into the commercially available pSG5 backbone (Stratagene Inc.). The pSG5 plasmid contains ampicillin and kanamycin as a selection marker for bacteria. This construct also contains F1 filamentous phage origin and SV40 promoter for better expression. The 584 base pair EPO fragment was cloned into the NCO/Bam H1site site of pSG5. The size of this vector was about 4.6 kb.

A second EPO vector was generated which comprised the EPO gene inserted into the commercially available pCDNA3.1 backbone (Invitrogen Life Technologies). This particular construct has the antibiotic Neomycin as a selection marker for mammalian cells.

Each of the EPO vectors was transfected into human chondrocytes using FuGENE 6, a commercially available lipid transfection agent (Roche Diagnostics Corporation). Primary human chondrocytes were passaged once, then seeded onto 35 mm plates at a density of 250,000 cells/plate in 10% FBS containing DMEM. The transfection reagents were combined in serum free medium at a ratio of 3 µl FuGENE to 1 µg plasmid and incubated for 15 minutes at room temperature. The resulting transfection mixture was then added dropwise to the chondrocyte plates, with a total of 1.0 µg of EPO plasmid added to each plate. The cell cultures were incubated at 37° C. Supernatant was collected, in aliquots of 0.5 ml, at 20, 48, 72 and 96 hours and stored at 4° C.

For this experiment, two control samples were prepared. The first control comprised chondrocytes which were transfected with a gene encoding an EPO mimetibody. The second control comprised cells to which no reagents were added. The above transfection procedure was repeated for human and bovine chondrocytes, with similar cell density, reagent concentrations and control conditions.

Expression of EPO was determined by measuring the supernatant EPO concentration synthesized by the chondrocytes using a commercially available ELISA kit which is specific to EPO (Quantikine IVD, R&D Systems Inc.). Absorption at 450 nm was measured to determine the amount of bound protein on the ELISA plates.

Figure 13A:
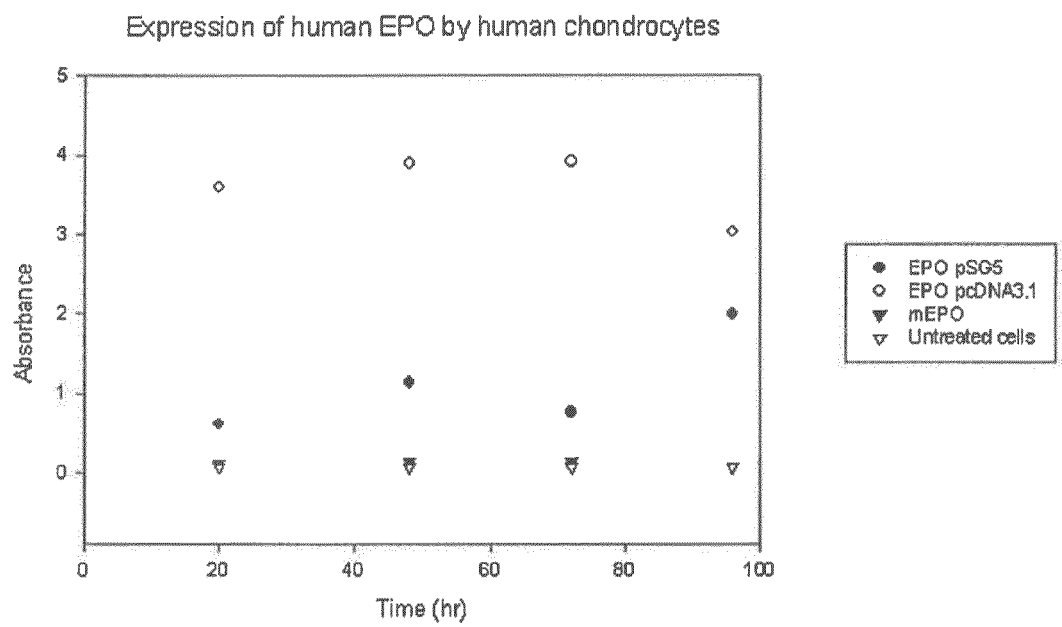
FIG. 13A is a graph showing expression of EPO from human chondrocytes.
Figure 13B:
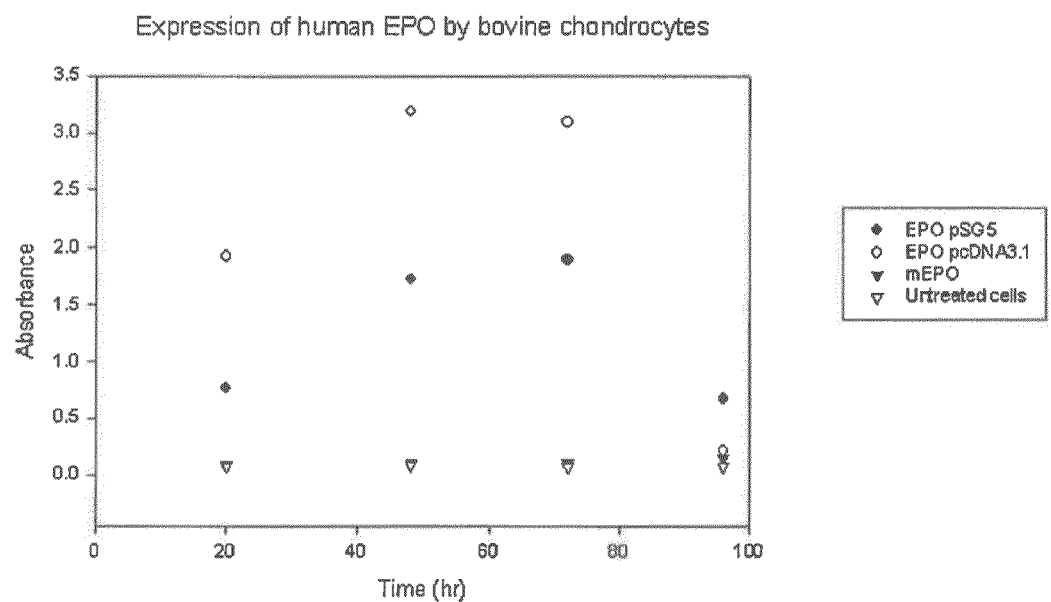
FIG. 13B is a graph showing expression of EPO from bovine chondrocytes.

FIGS. 13a and b shows that, for both human and bovine chondrocytes, neither control samples exhibited significant EPO expression, while both of the EPO transfection constructs resulted in significant EPO expression. Expression of human EPO by both human and bovine chondrocytes demonstrates the feasibility of allogeneic and xenogenic approaches to chondrocyte-based in vivo therapeutic delivery.

Example 4

In Vitro Transfection of Human Chondrocyte Cells and Expression of EPO Mimetibody This example described the techniques used to transfect chondrocytes with a therapeutic agent, the EPO mimetibody (mEPO). This compound is designed to mimic the binding region of the EPO protein, thereby providing the same therapeutic function as EPO when it attaches to the EPO receptor and activates it.

A construct was developed comprising the mEPO gene inserted into the commercially available pCDNA3.1 backbone (Invitrogen Life Technologies). This particular construct has the antibiotic, Neomycin as a selection marker for mammalian cells, and Ampicillin as a selection marker for bacteria. The size of this vector construct was about 6 kb. Another construct was developed comprising the mEPO gene inserted into the commercially available pCEP4 backbone (Invitrogen Life Technologies). This construct has hygromycin as a selection marker for mammalian cells, and contains EBV replication origin and nuclear antigen (EBNA-1) for better expression. The size of this vector is about 11 kb.

Each plasmid encoding mEPO was transfected into human chondrocytes using the method outlined in Example 3. Control samples comprised chondrocytes transfected with human EPO, as well as cells to which no reagents were added.

Figure 14:
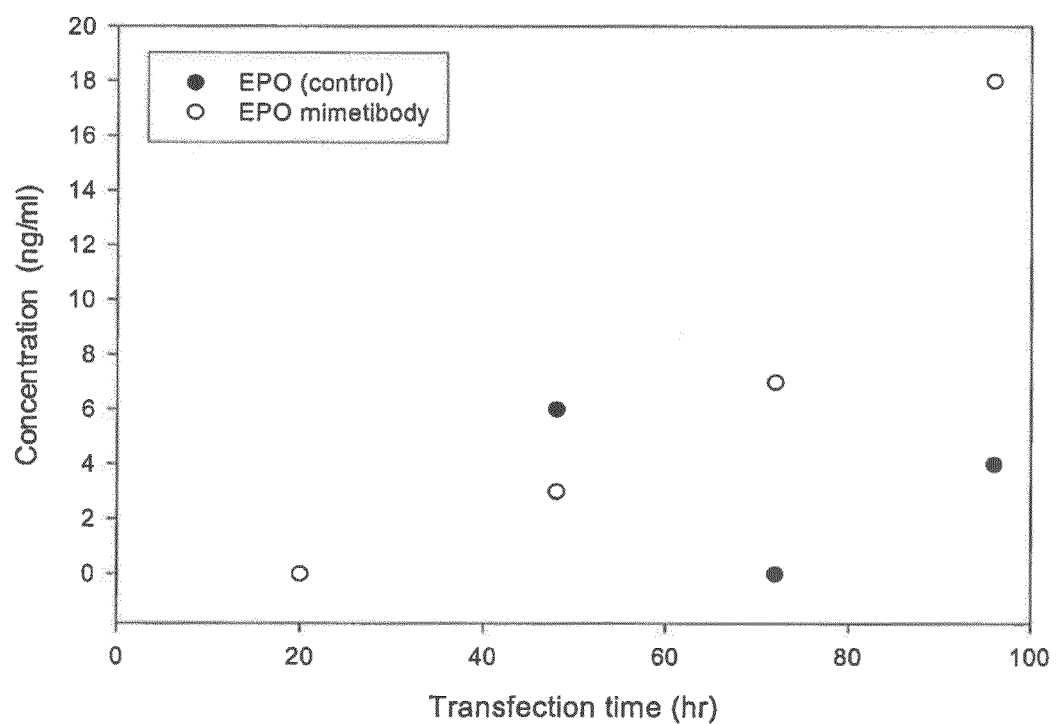
FIG. 14 is a graph showing expression of EPO mimetibody from human chondrocytes.

Expression of mEPO was measured using an ELISA which is specific to the human IgG region of the mimetibody. After 96 hours of transfection, EPO mimetibody expression was detected at a level of 18 ng/ml. As shown in FIG. 14, this expression level was substantially higher than the baseline mEPO level measured for control samples. Collectively, these results demonstrate that chondrocytes can be used to express a therapeutic agents such as EPO and mEPO.

Example 5

Creating Chondrocyte-Gel Substrates

This Example describes how to formulate biological gel matrix substrates comprising genetically altered chondrocytes that express a therapeutic agent. Chondrocytes growing in monolayer (FIG. 15A) were released from the culture dish using trypsin/EDTA. The cells were counted and suspended in low melting agarose at 40° C. prepared in serum free medium such that the final concentration of cells was 100, 000/ml of agarose gel. 3 ml of gel was dispensed into a 30 mm dish and allowed to set at room temperature. The gel was then overlayed with an equal volume of 10% FBS containing culture medium. The media is replenished every 2 to 3 days and cultures maintained for several weeks. After a few weeks, colonies of differentiating chondrocytes can be observed (FIG. 15B). The gels were fixed in formalin 6 weeks after initial suspension and stained with alcian blue. Cartilage matrix deposited by the chondrocytes stains blue and indicates cartilage differentiation (FIG. 15C). Monitoring of therapeutic protein expression could be performed by sampling the culture media overtime. Establishing a delivery dose from such agarose suspended chondrocytes could be done by harvesting different size disks generated for example with a biopsy punch.

Example 6

Use of Chondrocytes to Express a EPO or mEPO in a Non-Typical Chondrocyte Environment for a Blood Disorder This example describes the use chondrocytes that have been genetically altered to express EPO or mEPO in an in vivo system. The chondrocytes were genetically altered as described in Examples 3 and 4 to express EPO or mEPO, and placed into biological gel matrix substrates as described in Example 5. Slices of the solid gel, or a liquid gel that solidifies on contact, can be placed into an animal model of anemia (See Osborn et al, Supra), and the amelioration of anemia was observed by measuring the hemocrit levels of the blood.

Example 7

Use of Chondrocytes to Express Therapeutic Agent in a Non-Typical Chondrocyte Environment for an Autoimmune Disorder This example describes the use chondrocytes that have been genetically altered to express a therapeutic agent for amelioration of an autoimmune disorders, such as expressing insulin an animal model for diabetes.

The chondrocytes were genetically altered as described in Example 2 to express the insulin gene, and placed into biological gel matrix substrates as described in Example 5. Slices of the solid gel, or a liquid gel that solidifies on contact, can be placed (e.g., into the pancreas) in an animal model of insulin (See e.g., Wong et al. Supra), and changes in the blood glucose levels can be observed.

Example 8

Use of Chondrocytes to Express a GABA in a Non-Typical Chondrocyte Environment for Neurodegenerative Disorder This example describes the use chondrocytes that have been genetically altered to express GABA an animal model for Parkinson's disease. The chondrocytes were genetically altered as described in Example 2 to express GABA, and placed into biological gel matrix substrates as described in Example 5. Slices of the solid gel, or a liquid gel that solidifies on contact, can be placed into a region of the brain (e.g., subthalmic nucleus) in a model for Parkinson's disease (See e.g., Bjorklund et al., Supra), and the amelioration of Parkinson's symptoms can be observed be monitoring the behavioral changes in the animal (e.g., by a maze test).

Example 9

Chondrocytes Contained in Agarose Gel

This example demonstrates the superior ability of chondrocytes to survive in large devices. Three different cell types, chondrocytes, ligament cells and dermal fibroblasts, were encapsulated in large alginate capsules. Cells at a density of $10^6$ cells were encapsulated in cylindrical alginate gel plugs (Alginic acid sodium salt, Fluka #71238) 1 cm diameter×2 cm length and kept in either Dulbecco's Modified Eagle Medium (DME or DMEM; Gibco/Invitrogen #11995-040) with 10% fetal bovine serum (FBS) or DME/ITS (ITS—Insulin, Transferrin, Selenium—Gibco/Invitrogen #51500-056) media for several weeks at 37° C. The cells were then stained with a live/dead dye (Molecular Probes #L3224) that stains the live cells in green and the dead cells in red.

A qualitative visual assessment of the results (see FIGS. 8A-10B) show that the chondrocyte cultures have a higher proportion of green cells than red cells demonstrating their enhanced survivability in large cylindrical constructs.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A method for modifying an environment of a target cell associated with a disorder using a genetically altered chondrocyte, comprising:
   fully enclosing a genetically altered chondrocyte altered to express a therapeutic agent within one or more discrete semi-permeable containers, each having at least one chamber, the containers configured to retain the genetically altered chondrocyte while allowing passage of the therapeutic agent; and
   delivering the one or more containers to the environment of a target cell associated with a disorder;
   wherein the therapeutic agent is expressed and released from the one or more containers.

2. The method of claim 1, wherein the target cell associated with the disorder is in an atypical chondrocyte environment.

3. The method of claim 2, wherein the atypical chondrocyte environment is in an organ selected from the group consisting of the brain, heart, liver, kidney, gastro-intestinal tract, spleen, smooth muscles, skeletal muscles, eye, ganglions, lungs, gonads, and pancreas.

4. The therapeutic system of claim 2, wherein the atypical chondrocyte environment is an aqueous environment selected from the group consisting of blood and plasma.

5. The method of claim 1, wherein the target cell associated with the disorder is in a typical chondrocyte environment.

6. The method of claim 5, wherein the typical chondrocyte environment is selected from the group consisting of bone, tendon and cartilage.

7. The method of claim 1, wherein the target cell associated with the disorder is a cell selected from the group consisting of a cell associated with a blood disorder, a cell associated with a cardiovascular disorder, a cell associated with an endocrine disorder, a cell associated with an autoimmune disorder, a cell associated with a neurological disorder, a cell associated with a skin disorder, a cell associated with fertility disorder, and a cell associated with reproduction.

8. The method of claim 1, wherein the one or more containers comprise a rigid material.

9. The method of claim 1, wherein the one or more containers further include at least one port.

10. The method of claim 1, wherein the genetically altered chondrocyte, is genetically altered to produce a therapeutic agent selected from the group consisting of a protein, an agonist or an antagonist of an antibody, an antigen, a hormone, an anti-inflammatory agent, an antiviral agent, an antibacterial agent, a growth factor, a cytokine, an oncogene, a tumor suppressor, a transmembrane receptor, an adhesion molecule, a neurotransmitter, a morphogenetic protein, a differentiation factor, an enzyme, and an extracellular matrix protein.

11. The method of claim 1, wherein the therapeutic agent is an Erythropoietin protein.

12. The method of claim 1, wherein the therapeutic agent is an Erythropoietin mimetibody.

* * * * *